(12) United States Patent
Bumelis

(10) Patent No.: US 8,709,757 B2
(45) Date of Patent: Apr. 29, 2014

(54) METHOD FOR PRODUCING INTERFERON ALPHA 5

(75) Inventor: Vladas Algirdas Bumelis, Vilnius (LT)

(73) Assignee: Digna Biotech, S.L., Pamplona (Navarra) (ES)

( * ) Notice: Subject to any disclaimer, the term of this patent is extended or adjusted under 35 U.S.C. 154(b) by 0 days.

(21) Appl. No.: 13/576,068

(22) PCT Filed: Jan. 31, 2011

(86) PCT No.: PCT/ES2011/070057
§ 371 (c)(1),
(2), (4) Date: Jul. 30, 2012

(87) PCT Pub. No.: WO2011/092367
PCT Pub. Date: Aug. 4, 2011

(65) Prior Publication Data
US 2012/0309057 A1 Dec. 6, 2012

(30) Foreign Application Priority Data

Feb. 1, 2010 (EP) ..................................... 10382019

(51) Int. Cl.
*C12P 21/04* (2006.01)
*C12N 1/20* (2006.01)
*C12N 1/21* (2006.01)
*C07K 14/56* (2006.01)
*A61K 38/21* (2006.01)

(52) U.S. Cl.
USPC ................ 435/69.51; 435/252.33; 435/252.8; 530/351; 424/85.7

(58) Field of Classification Search
None
See application file for complete search history.

(56) References Cited

U.S. PATENT DOCUMENTS

| | | | |
|---|---|---|---|
| 4,511,502 A | 4/1985 | Builder et al. | |
| 4,569,908 A | 2/1986 | Mark et al. | |
| 4,765,903 A | 8/1988 | D'Andrea et al. | |
| 4,845,032 A | 7/1989 | Obermeier | |
| 2006/0188477 A1* | 8/2006 | Prieto Valtuena et al. | ... 424/85.7 |
| 2008/0132681 A1* | 6/2008 | Hays et al. | ................... 530/351 |

FOREIGN PATENT DOCUMENTS

| | | |
|---|---|---|
| EP | 1310559 A1 | 5/2003 |
| EP | 1990349 A1 | 11/2008 |
| WO | 9721829 A1 | 6/1997 |
| WO | 2005087940 A1 | 9/2005 |

OTHER PUBLICATIONS

Kensy, Frank, et al.; "Scale-ip from microtiter plate to laboratory fermenter: Evaluation by online monitoring techniques of growth and protein expression in *Escherichia coli* and *Hansenula polymorpha* fermentations," Microbial Cell Factories, 2009, pp. 1-15, vol. 8.
Khalilzadeh, R., et al.; "Process development for production of recombinant human interferon-y expressed in *Escherichia coli*," J. Ind. Microbiol. Biotechnol., 2004, pp. 63-69, vol. 31.
Korz, D.J., et al; "Simple fed-batch technique for high cell density cultivation of *Escherichia coli*," Journal of Biotechnology, 1995, pp. 59-65, vol. 39.
Pack, Peter, et al; "Improved Bivalent Miniantibodies, with Identical Avidity as Whole Antibodies, Produced by High Cell Density Fermentation of *Escherichia coli*," Bio/technology, 1993, pp. 1271-1277, vol. 7.
International Search Report, May 31, 2011.

* cited by examiner

*Primary Examiner* — Robert Landsman
*Assistant Examiner* — Bruce D Hissong
(74) *Attorney, Agent, or Firm* — Tristan A. Fuierer; Andrew D. Gerschutz; Moore & Van Allen, PLLC

(57) ABSTRACT

A process for producing an interferon alpha 5 (IFNa5) protein by expression in an IFNa5 producing *Escherichia coli* host cell, wherein incorporation of an extra methionine residue in the N-terminal end of the polypeptide chain is minimized as well as the generation of its oxidized species is disclosed. The IFNa5 protein can be purified by an efficient process to render a biologically active IFNa5.

20 Claims, 13 Drawing Sheets

Mature Structure with Codon Optimisation

PCR amplification of the DNA fragment coding IFN alpha-5
↓
DNA fragment ligation into intermediate plasmid
↓
Confirmation of the nucleotide sequence
↓
Subcloning into pET21b(+) vector
↓
Transformation to *E. coli* BL21(DE3) strain
↓
Confirmation of the plasmid structure by restriction analysis
↓
Establishment of the clones producing IFN alpha-5

Fig 1

```
1    atg tgt gat ctg cag acc cac tcc ctg tct aac agg agt act gtg atg atg atg gca
      M   C   D   L   Q   T   H   S   L   S   N   R   S   T   V   M   M   M   A 61   cag atg gtt ggt atc tct cct ttc tcc tgc ctg aag gac aga cat gac ttt gga ttt cct
      Q   M   G   I   S   P   F   S   C   L   K   D   R   H   D   F   G   F   P 121  cag gag gag ttt gat ggc aac cag ttc cag aag gct caa gcc atc tct gtc ctc cat gag
      Q   E   E   F   D   G   N   Q   F   Q   K   A   Q   A   I   S   V   L   H   E 181  atg atc cag cag acc ttc aat ctc ttc agc aca aag gac tca tct atc act tgg gat gag
      M   I   Q   Q   T   F   N   L   F   S   T   K   D   S   S   I   T   W   D   E 241  aca ctt cta gac aaa ttc tac act gaa ctt tac cag cag ctg aat gac ctg gaa gcc tgt
      T   L   L   D   K   F   Y   T   E   L   Y   Q   Q   L   N   D   L   E   A   C 301  atg atg cag gag gtt gga gtg gaa gac act cct ctg atg aat gtg gac tct atc ctg act
      M   M   Q   E   V   G   V   E   D   T   P   L   M   N   V   D   S   I   L   T 361  gtg aga aaa tac ttt caa aga atc act ctc tat ctg aca gag aag aaa tac agc cct tgt
      V   R   K   Y   F   Q   R   I   T   L   Y   L   T   E   K   K   Y   S   P   C 421  gca tgg gag gtt gtc aga gca gaa atc atg aga tcc ttc tct tta tca gca aac ttg caa
      A   W   E   V   V   R   A   E   I   M   R   S   F   S   L   S   A   N   L   Q 481  gaa cgt tta cgg cgg aag gaa tga    604   SEQ ID NO: 6
      E   R   L   R   R   K   E   -           SEQ ID NO: 1
```

Fig.4

METHOD FOR PRODUCING INTERFERON ALPHA 5

CROSS-REFERENCE TO RELATED APPLICATIONS

This application is filed under the provisions of 35 U.S.C. §371 and claims the priority of International Patent Application No. PCT/ES2011/070057 filed on 31 Jan. 2011 entitled "Method for Producing Interferon Alpha 5" in the name of Vladas Algirdas BUMELIS, which claims priority of EP 10382019.7 filed on 1 Feb. 2010, both of which are hereby incorporated by reference herein in their entirety.

FIELD OF THE INVENTION

The present invention relates to a process for producing an interferon alpha 5 (IFNa5) protein by expression in an IFNa5 producing *Escherichia coli* host cell, wherein incorporation of an extra methionine residue in the N-terminal end of the polypeptide chain is minimized as well as the generation of its oxidised species. The IFNa5 protein can be purified by an efficient process to render a biologically active IFNa5.

BACKGROUND OF THE INVENTION

Interferons (IFNs) are a group of naturally-produced pleiotropic glycoproteins, known as cytokines, secreted from different kinds of cells (epithelial cells, fibroblasts, lymphocytes, macrophages) by induction from a series of stimulations (virus, bacteria, cells, tumours and macromolecules) and endowed with antiviral, anti-proliferative, and immuno-modulatory properties as well as an analgesic action. Following its endogenous production or its administration, the interferon interacts with the specific receptors on the cells surface and starts the transduction of the signal through the cytoplasm until the nucleus, inducing the expression of genes which codify for specific proteins having antiviral and immuno-stimulating activity. The medical potential of IFNs has been recognized, as demonstrated by the approval of some different types of IFNs for use in humans, such as IFN1a (Rebif, Avonex), IFN1b (Betaseron), as drugs for the treatment of multiple sclerosis, and recombinant human IFNa2a (Roferon A) and IFNa2b (Intron A), as drugs for the treatment of malignant (cancer) and viral diseases.

Based on the type of receptor through which IFNs signal, human IFNs have been classified into three major types, namely, (i) IFN type I [all type I IFNs bind to a specific cell surface receptor complex known as the IFN-alpha receptor (IFNAR)—type I IFNs in humans are IFN alpha (IFN-α), IFN beta (IFN-β) and IFN omega (IFN-ω)], (ii) IFN type II [type II IFN binds to a IFN-gamma receptor (IFNGR)—type II IFN in humans is IFN gamma (IFN-γ)], and IFN type III [type III IFNs signal through a receptor complex consisting of IL10R2 and IFNLR1]. IFNs alpha and beta, known as type I IFNs, are structurally correlated, stable at acid pH and compete for the same cell-receptor (IFNAR).

At present, IFNs alpha, beta and gamma can be manufactured under recombinant form with the double advantage of getting much higher amounts of product compared to those obtained through the isolation from natural sources (leukocytes, fibroblasts, lymphocytes) and of reducing the complexity of the processes of purification and check of the safety of the product. In fact, most of the marketed pharmaceutical grade recombinant IFN is produced and purified from *Escherichia coli*.

The *E. coli* recombinant protein expression system has been, and still is, the system of choice for the production of IFN. Indeed, IFN genes do not have introns, and the protein products are generally not glycosylated. Furthermore, *E. coli* can grow rapidly to high cell densities, and strains used for recombinant protein production have been genetically modified so that they are generally regarded as safe for large-scale fermentation.

The expression of IFN cDNA was achieved directly in *E. coli* soon after it was first cloned [Goedell et al. Nature., 287, 411-416, 1980; Pestka, S. Arch. Biochem. Biophys., 221 (1), 1-37, 1983; Mizoguchi et al. DNA., 4, 221-32, 1985; Pestka et al. Ann. Rev. Biochem., 56, 727-777, 1987; Baron and Narula. Critical reviews in Biotechnology, 10 (3), 179-190, 1990]. In fact, IFN alpha (IFNa) has been one of the first proteins to be produced by means of *E. coli* with the DNA recombinant technology [Derynck et al., Nature, 287, 193-197, 1980; Nagata et al., Nature, 284, 316-320, 1980].

However, the expression of IFNs in *E. coli* shows some problems. IFNs expressed in large amount in *E. coli* often precipitate into insoluble aggregates called inclusion bodies (IBs) [Swaminathan et al., Prot Express. Purif., 15, 236-242, 1999; Bedarrain et al., Biotechnol. Appl. Biochem., 33, 173-182, 2001; Srivasta et al. Prot. Express. Purif 41, 313-322, 2005] that are, in general, misfolded proteins and thus biologically inactive [Villaverde and Carrio, Biotechnol. Lett., 25, 1385-1395, 2003]. To get such proteins under native form it is necessary to submit said IBs to a denaturation phase followed by a renaturation phase, oxidizing, in case that disulfide bridges have to be formed as in the natural protein. Further, the incorporation of an extra methionine residue at the N-terminal end of the target protein sequence (e.g., an IFN) is a characteristic feature of protein expression in *E. coli*. As it is known, methionine residues distributed within the sequence of a protein are prone to oxidation. Such process may occur during the process for producing the protein or the pharmaceutical composition comprising said protein (if it can be used as a drug, e.g., an IFN) and is more pronounced during long-term storage at elevated temperatures.

Although several methods of production and purification of IFNs in bacteria as IBs have been developed [e.g., Thatcher and Panayotatos, Methods Enzymol. 119, 166-177, 1986; U.S. Pat. No. 4,511,502; U.S. Pat. No. 4,765,903; U.S. Pat. No. 4,845,032; EP 1310559; or EP 1990349], there are further factors which may present obstacles for successful production and purification of IFNs, namely, an IFNa of therapeutical degree, such as the incorporation of an extra methionine residue at the N-terminus of the target IFN and the generation of its oxidised species which have to be removed (if the product is to be used as a drug) thus reducing the overall yield in the production of IFN, increasing the complexity of the purification process and rendering the process for production and purification of alpha IFNs of therapeutical degree in a laborious process.

Accordingly, there remains a need for a method that enables the production of IFNa, particularly, IFNa5, of therapeutical degree from *E. coli* host cells in a high yielding and cost-effective manner.

SUMMARY OF THE INVENTION

Inventors have now found, surprisingly, that the concentration of microelements (trace elements) in the fermentation medium plays an important role in the post-translational modifications of IFNa5. Thus, controlling the concentration of microelements in the fermentation medium, it is possible to minimize the incorporation of an extra methionine residue in the N-terminal end of an IFNa5 produced in an IFNa5 producing *E. coli* host cell as well as to minimize the generation of its oxidised species, what increases the production yield and simplifies the purification process thus rendering a process for the production and purification of an IFNa5, namely, an IFNa5 of therapeutical degree, produced in an IFNa5 producing *E. coli* host cell in a cost-effective less complex process.

Effectively, Example 4 shows that the formation of the oxidized methionilated human IFN alfa-5 (hIFNa5) form is eliminated and the amount of the acetylated hIFNa5 forms is reduced twice (i.e., in half), when 1 liter (L) of the carbon feed solution contains from about 3.0 mL to about 3.7 mL of a microelements stock solution, and, preferably, the average specific culture growth rate ($\mu$) after induction is equal to or higher than 0.17.

Therefore, in an aspect, the invention relates to a process for producing an interferon alpha 5 (IFNa5) protein by expression in an IFNa5 producing *Escherichia coli* host cell, which comprises:

a) providing an IFNa5 producing *E. coli* host cell;
b) culturing the IFNa5 producing *E. coli* host cell under conditions effective to express said IFNa5 protein by said recombinant IFNa5 producing *E. coli* host cell in a fermentation medium, with the addition of a carbon feed solution, wherein
said fermentation medium is free of components from animal origin or yeast origin, and
said carbon feed solution comprises a carbon source and from about 3.0 to about 3.7 mL of a solution of microelements per liter of added carbon feed solution; and
c) isolating, and optionally purifying, the expressed IFNa5 protein.

In a particular embodiment, said *E. coli* host cell is an *E. coli* protease deficient strain, such as the *E. coli* lon⁻/ompT⁻ protease deficient host strain, preferably an *E. coli* BL21 strain, most preferably an *E. coli* BL21 (DE3) strain.

In another particular embodiment, when the *E. coli* strain is an *E. coli* BL21 (DE3) strain, the conditions of step b) comprise induction with IPTG.

In another particular embodiment, step c) of isolating and purifying the expressed IFNa5 protein comprises successively, after lysis of the *E. coli* host cells, isolating said IFNa5 protein in the form of inclusion bodies (IBs) by subjecting said IBs to solubilization, and the resulting mixture to an oxidizing renaturation and to a progressive series of chromatography comprising:

1) subjecting a mixture comprising renatured IFNa5 to a hydrophobic interaction chromatography;
2) subjecting the solution obtained at step 1) to an anion-exchange chromatography;
3) subjecting the solution obtained at step 2) to a first cation-exchange chromatography; and
4) subjecting the solution obtained at step 3) to a second cation-exchange chromatography, wherein said solution is, optionally, diluted with a buffer comprising methionine, in order to obtain a purified IFNa5.

In a particular embodiment, said IFNa5 is, preferably, a human IFNa5 (hIFNa5).

BRIEF DESCRIPTION OF THE DRAWINGS

FIG. 1 shows the flowchart of construction of an IFNa5 producing strain.

FIG. 4 shows the complete nucleotide sequence of human IFN alpha-5 (hIFNa5) coding fragment optimized for expression in *E. coli* (SEQ ID NO: 6) by replacing some codons with the least frequently used codons used in *E. coli*. Nucleotide substitutions are underlined. The amino acid sequence in this Figure corresponds to SEQ ID NO: 1.

DETAILED DESCRIPTION OF THE INVENTION

Definitions

Figure 2:
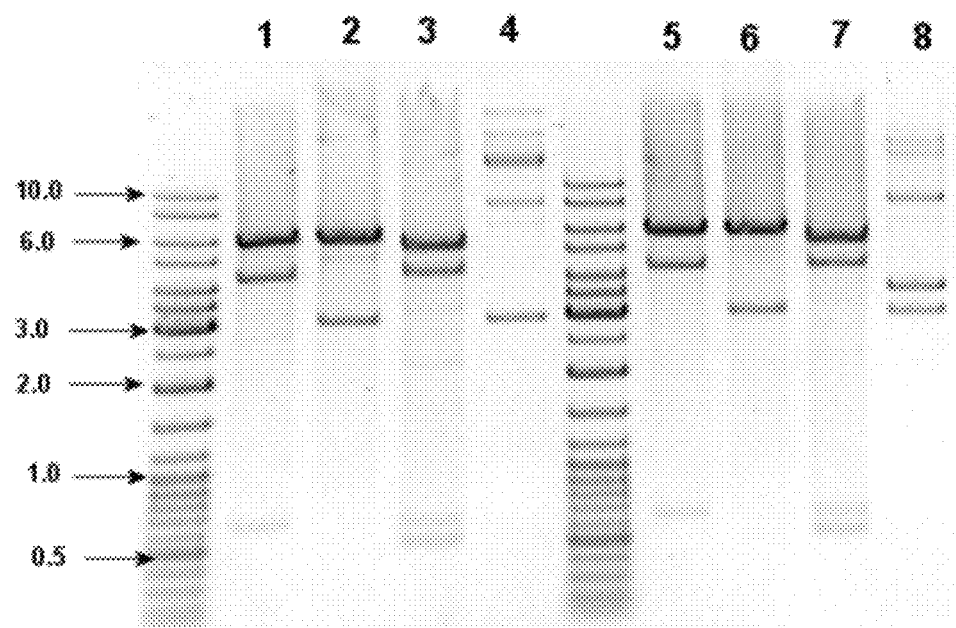
FIG. 2 shows the results of the restriction analysis of primary plasmid DNA pET28-IFN alpha-5. Lanes 1-3 and 5-7: restriction analysis of pET28-IFN alpha-5; lanes 1 and 5: pET28-IFN alpha-5/BamHI; lanes 2 and 6: pET28-IFN alpha-5/NdeI; lanes 3 and 7: pET28-IFN alpha-5/NdeI+BamHI; lanes 4 and 8: pET28-IFN alpha-5, uncleaved. Size of marker DNA (Gene Ruler DNA Ladder Mix, Fermentas, Lithuania) bands in kilobase pairs (kbp) is indicated.

In order to facilitate the comprehension of the present invention, the meaning of some terms and expressions as used in the context of the invention is hereby provided.

As used herein the term "interferon alpha 5" (or "IFN alpha 5" or "IFNa") refers to a protein produced by leukocytes which apparently is mainly involved in innate immune response against viral infection, capable of binding to a specific cell surface receptor complex known as the IFNa receptor (IFNAR).

IFNa5 proteins are described, for instance, in WO 83/02459 (hIFNa5).

The term "IFNa5" includes proteins having (i) an amino acid sequence that is at least substantially identical to the amino acid sequence of a native IFNa5 protein and (ii) a biological activity that is common to a native IFNa5. Substantial identical amino acid sequence means that the sequences are identical or different by one or more amino acid alterations (i.e., deletions, additions, substitutions) that do not produce an adverse functional dissimilarity between the synthetic protein and the native IFNa5, for example, IFNa5 proteins having at least 70% of identity with one of the cited IFNa5 proteins. X % of identity between an IFNa5 protein (P) and an IFNa5 protein of reference (R), means that when the two sequences are aligned, X % of the amino acids of P are identical to the corresponding amino acid in sequence R or are replaced by an amino acid of the same group, such as:

- Amino acids with nonpolar R groups: Alanine, Valine, Leucine, Isoleucine, Proline, Phenylalanine, Tryptophan, Methionine;
- Amino acids with uncharged polar R groups: Glycine, Serine, Threonine, Cysteine, Tyrosine, Asparagine, Glutamine;
- Amino acids with charged polar R groups (negatively charged at pH 6.0): Aspartic acid, Glutamic acid;
- Basic amino acids (positively charged at pH 6.0): Lysine, Arginine, Histidine (at pH 6.0);
- Amino acids having phenyl groups: Phenylalanine, Tryptophan, Tyrosine.

Particularly preferred conservative substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NH2 can be maintained.

These percentages of sequence identity may be obtained by using the BLAST program (blast2seq, default parameters) [Tatutsova and Madden, FEMS Microbiol. Lett., 174, 247-250 (1990)].

As used herein the term "IFNa5 producing *E. coli* host cell" refers to an *E. coli* host cell that has been genetically engineered to produce a protein that possesses biological activity associated with an IFNa5. In a particular embodiment, the *E. coli* host cell is an *E. coli* protease deficient strain, such as the *E. coli* Ion$^-$/ompT$^-$ protease deficient host strain, preferably an *E. coli* BL21 strain, most preferably an *E. coli* BL21 (DE3) strain.

As used herein the term "biological activity of an IFNa5" refers to any biological activity of said IFNa5 including the therapeutic activity of said IFNa5. WO 83/02459 discloses that IFNa5 exhibits antiviral activity against DNA and RNA viruses, cell growth activity and an ability to regulate the production of intracellular enzymes and other cell-produced substances; accordingly, it is expected that IFNa5 may be used to treat viral infections (e.g., chronic hepatitis B infection), tumors and cancer.

As used herein the expression a fermentation medium is "free of components from animal origin or yeast origin" means that there is no risk of transmitting agents causing Spongiform Encephalopathy via medicinal products, there is no any evidence of BSE contamination or cases of vCJD associated with pharmaceutical products. Product is free from trace amount of contaminating proteins from yeast cells.

Process for Producing an IFNa5

In an aspect, the invention relates to a process for producing an interferon alpha 5 (IFNa5) protein by expression in an IFNa5 producing *Escherichia coli* host cell, hereinafter the "process of the invention", which comprises:

a) providing an IFNa5 producing *E. coli* host cell;
b) culturing the IFNa5 producing *E. coli* host cell under conditions effective to express said IFNa5 protein by said recombinant IFNa5 producing *E. coli* host cell in a fermentation medium, with the addition of a carbon feed solution, wherein
    said fermentation medium is free of components from animal origin or yeast origin, and
    said carbon feed solution comprises a carbon source and from about 3.0 to about 3.7 mL of a solution of microelements per liter of added carbon feed solution; and
c) isolating, and optionally purifying, the expressed IFNa5 protein.

The recombinant IFNa5 which may be produced according to the process of the invention have been previously defined. In a particular embodiment, said recombinant IFNa5 which may be produced according to the process of the invention is an IFNa5 protein which is substantially identical to the native IFNa5, i.e., a protein that is produced by an IFNa5 producing *E. coli* host cell that has been transformed with an IFNa5 encoding gene or a modification thereof that encodes a protein having (1) an amino acid sequence that is at least substantially identical to the amino acid sequence of a native IFNa5 and (2) a biological activity that is common to a native IFNa5. In a preferred embodiment, said IFNa5 is hIFNa5.

In a more particular embodiment, the recombinant IFNa5 produced according to the process of the invention is an IFNa5 having the amino acid sequence shown in SEQ ID NO: 1 (FIG. 4) which corresponds to the mature hIFNa5 having an extra methionine residue at the N-terminal end of the polypeptide chain.

According to the process of the invention, an IFNa5 producing *E. coli* host cell is provided [step a)]. Although, in principle, any *E. coli* strain can be used in the process of the invention, in a preferred embodiment, the *E. coli* host cell is an *E. coli* protease deficient strain, such as the *E. coli* Ion$^-$/ompT$^-$ protease deficient host strain, preferably an *E. coli* BL21 strain, most preferably an *E. coli* BL21 (DE3) strain.

The IFNa5 producing *E. coli* host cell can be obtained by conventional methods and protocols for cloning and expressing an IFNa5 [e.g., Sambrook et al. Molecular cloning: A Laboratory Manual. Second ed., CSH Laboratory, Cold Spring Harbor, 1989; Current Protocols in Molecular Biology, vol. 1-3 (Ausubel F. M. et al., ed.) John Wiley & Sons, Inc., Brooklyn, N.Y., 1994-1998]. In a particular embodiment, the cloning and expression of an IFNa5 encoding gene and the construction of the bacterial strain producing recombinant IFNa5 protein (i.e., the IFNa5 producing *E. coli* host cell) can be performed according to a method which comprises cloning of the cDNA gene encoding an IFNa5, modification of the DNA sequence of said gene to optimize its expression in *E. coli*, construction of the expression plasmid, transformation of the selected plasmid into a suitable *E. coli* strain and selection of the expression/induction conditions. Example 1 discloses the construction of a hIFNa5 producing *E. coli* host cell.

In a particular embodiment, when the *E. coli* host cell is an *E. coli* protease deficient strain, such as the *E. coli* BL21 (DE3) strain, said host cell is transformed with a vector comprising a sequence encoding the IFNa5 protein under the control of an inducible promoter; in that case, the expression of the protein requires the addition of an inducer, such as, for example, isopropyl-β-D-thiogalactopyranoside (IPTG). Thus, according to a particular embodiment, when the *E. coli* host cell is an *E. coli* BL21 strain, such as an *E. coli* BL21 (DE3) strain, the conditions of step b) comprise induction with IPTG.

In step b) of the process of the invention, the IFNa5 producing *E. coli* host cell is cultured under conditions effective to express said IFNa5 protein by said recombinant IFNa5 producing *E. coli* host cell in a fermentation medium, with the addition of a carbon feed solution, wherein
said fermentation medium is free of components from animal origin or yeast origin, and
said carbon feed solution comprises a carbon source and from about 3.0 to about 3.7 mL of a solution of microelements per liter of added carbon feed solution; and The effective conditions in which the IFNa5 producing *E. coli* host cell has to be cultured to express said IFNa5 protein are, in general, known by the skilled person in the art. Said conditions include a fermentation medium comprising a nitrogen source, a carbon source and a metals source, suitable for the *E. coli* host cell to be cultured with the proviso, according to the present invention, that the fermentation medium is free of components from animal origin or yeast origin such as a synthetic chemical fermentation medium.

In a particular embodiment, ammonium phosphate dibasic and ammonia, alone or in combination, can be used as a nitrogen source. In another particular embodiment, the carbon source may be citric acid, glucose, or combinations thereof.

Example 2 discloses a fermentation medium for culturing a IFNa5 producing *E. coli* BL21 (DE3) strain, said medium comprising ammonium phosphate dibasic, magnesium sulfate, potassium dihydrogen phosphate, citric acid, D(+)-glucose and a microelements stock solution, wherein said microelements stock solution comprises microelements selected from the group of microelements consisting of iron, calcium, zinc, manganese, copper, cobalt, molybdenum, boron and combinations thereof. In a particular embodiment, said fermentation medium comprises a source of microelements selected from the group of sources of microelements consisting of iron (III) chloride, calcium chloride, zinc (II) sulfate, manganese (II) sulfate, copper (II) sulfate, cobalt (II) chloride, sodium molybdate, boric acid and combinations thereof. In a particular embodiment, the microelements (trace elements) stock solution comprises (in g/L): iron (III) chloride hexahydrate (30.0), calcium chloride dihydrate (4.05), zinc (II) sulfate heptahydrate (6.75), manganese (II) sulfate monohydrate (1.5), copper (II) sulfate pentahydrate (3.0), cobalt (II) chloride hexahydrate (1.14), sodium molybdate dihydrate (0.3) and boric acid (0.69) [Example 4].

Another feature of the process of the invention refers to the fact that the carbon feed solution comprises a carbon source and from about 3.0 to about 3.7 mL of a solution of microelements per liter of added carbon feed solution. The particulars of said microelements solution have been previously defined. In a particular embodiment, the carbon feed solution comprises a carbon source (e.g., citric acid and/or glucose), magnesium sulfate and, according to the invention, a concentrated microelements solution in a concentration of about 3.0 mL to about 3.7 mL of microelements solution per liter of carbon feed solution to be added. As mentioned above, Examples 2 and 4 disclose a microelements stock solution comprising microelements selected from the group of microelements consisting of iron, calcium, zinc, manganese, copper, cobalt, molybdenum, boron and combinations thereof in a particular embodiment, said microelements stock solution comprises iron (III) chloride, calcium chloride, zinc (II) sulfate, manganese (II) sulfate, copper (II) sulfate, cobalt (II) chloride, sodium molybdate, boric acid and combinations thereof. In a particular embodiment, the microelements stock solution included in a concentration of about 3.0 mL to about 3.7 mL of microelements solution per liter of carbon feed solution is the microelements stock solution disclosed in Example 2 and 4. Example 2 discloses the biosynthesis process of hIFNa5 by a producing strain.

Different studies performed by the inventors have shown the effect of microelements on post-translational modifications of recombinant IFNa5 (e.g, hIFNa5), namely, that the relative amount of oxidized-Met found in a purified API of a recombinant IFNa5 (e.g., a recombinant hIFNa5) produced in *E. coli* is in close relation with the amount of the "not processed methionine" at the N-terminal end of the polypeptide chain. In order to obtain less than 10% of said not processed methionine at the N-terminal end, the amount of oxidized-Met IFNa5 (determined by RP-HPLC) after refolding should constitute not more than 1%.

During the optimization of the recombinant hIFNa5 biosynthesis process, inventors observed that the concentration of microelements in the fermentation medium had an important effect on the post-translational modifications of hIFNa5. In fact, it was determined that the formation of the oxidized methionilated hIFNa5 form (oxidized-Met hIFNa5) is eliminated and the amount of acetylated hIFNa5 forms is reduced twice (in half), when 1 L of the carbon feed solution contains 3.0 mL-3.7 mL of said microelements stock solution or when it is within the limits of 0.0048 mL/L/o.u.-0.0070 mL/L/o.u. [o.u.: optical units].

In a particular embodiment, the process of the invention is performed under conditions in which the average "specific culture growth rate" (μ) after induction is equal to or higher than 0.17 [μ: ((In OD2−In OD1)/T2−T1), wherein OD is "optical density" (optical units, o.u.) and T is "time"]. Studies performed by the inventors have shown that culture growth and concentration of microelements are closely interdependent, especially when concentration of microelements is very low/nearly limiting. When concentration of microelements in the culture medium is lower than 0.95 mL/L final suspension volume (Example 4, Table 3) or less than 3.0 mL/L carbon feed solution, average μ after induction reaches just 0.121-0.158, i.e. less than 0.17 (M-83, M-84, M-85, M-86). However, when average μ after induction is less than 0.17, presence of oxidized methionilated IFNa5 form is practically warranted. Concentration of microelements in the culture medium higher than 1.23 mL/L final suspension volume results in quicker growth (M-89, M-90), bigger WCW and bigger amount of acetylated IFNa5 form+unknown protein. However, when average μ after induction is equal to or higher 0.17 the process works better until the concentration of microelements is higher than 0.123 mL/L final suspension volume or more than 3.7 mL/L carbon feed solution.

Step c) of the process of the invention comprises isolating, and optionally purifying, the expressed IFNa5 protein. In a particular embodiment, after lysing the IFNa5 producing *E. coli* host cells, the IFNa5 protein is isolated in the form of inclusion bodies (IBs) by subjecting said IBs to solubilization to render a mixture containing denatured IFNa5 which in turn is subjected to an oxidizing renaturation treatment to render a mixture comprising renatured IFNa5 which is then subjected to a purification process in order to obtain the corresponding purified IFNa5. In a particular embodiment, said IFNa5 is, preferably, hIFNa5.

To isolate and purify the IFNa5 expressed according to the process of the invention, the IFNa5 producing *E. coli* host cells are firstly lysed in order to isolate said recombinant IFNa5 in the form of inclusion bodies (IBs). Briefly, in a particular embodiment, the cell membranes of the IFNa5 producing *E. coli* host cells are lysed by using conventional techniques such as homogenization, sonication, or pressure cycling. Preferred methods include sonication or homogenization with a Poter's homogenizer (Teflon/glass). After the cells have been lysed, the IBs containing IFNa5 are separated from the liquid phase of the lysate, for example by centrifugation, and resuspended in an appropriate buffer solution. The IBs may be optionally washed to remove any water soluble *E. coli* proteins therein.

Subsequently, said IBs are solubilized in the presence of a solubilizing agent such as a chaotropic agent, e.g., a protein denaturant that dissociates hydrogen bonds and affects the tertiary and secondary structure of the protein causing its unfolding, generally in an aqueous buffer solution, in order to render a mixture comprising denatured IFNa5. Illustrative, non-limitative, examples of chaotropic agents include urea and guanidinium hydrochloride (GdmHCl), preferably guanidinium hydrochloride, a strong chaotropic agent which prevents carbamoylation of the polypeptide chain (what may occur if concentrated urea solution is used). The concentration of the chaotropic agent will depend upon the particular chaotropic agent used and the amount of cellular material present. Preferably a guanidinium hydrochloride solution having a concentration of 6-7 M, most preferably 6 M, is employed. The pH may be adjusted by adding suitable buffers, and, preferably, the pH will be above 7, typically, equal to or higher than about 8, preferably, equal to or higher than 8.6, more preferably, between 9.55 and 9.65, comprising a chaotropic agent. In general, in a preferred embodiment, IBs solubilization is performed at the same pH as for the refolding step thus avoiding additional adjustment of solubilizate pH for refolding step.

After solubilization of the IBs containing IFNa5, insoluble particulate matter is separated and discarded. Denatured IFNa5 present in the mixture containing denatured IFNa5 is renatured by diluting said mixture within a renaturing solution such as a renaturation buffer. In a particular embodiment, said renaturation buffer comprises a labilizing agent (e.g., L-arginine, etc.), a redox pair (e.g., GSH/GSSG, etc.), and, optionally, a chelating compound, in a buffer system having a pH above 7.0, typically, equal to or higher than about 8, preferably, equal to or higher than 8.6, more preferably, between 9.55 and 9.65. After renaturation, the resulting protein solution containing correctly folded IFNa5 is clarified by conventional techniques, e.g., centrifugation or filtration, in order to remove any remaining particulate matter. Then, if necessary, the pH of the clarified protein solution is adjusted to 8.0-8.20 with a suitable acid (e.g., HCl) and the mixture comprising renatured IFNa5 (protein solution) is then subjected to any suitable process for purifying IFNa5.

Although practically any IFNa5 purification process can be used, the invention further provides an efficient process for purifying an IFNa5 which comprises subjecting the renatured IFNa5 to a four-step chromatographic process comprising:

1) subjecting said mixture comprising renatured IFNa5 to a hydrophobic interaction chromatography;
2) subjecting the solution obtained at step 1) to an anion-exchange chromatography;
3) subjecting the solution obtained at step 2) to a first cation-exchange chromatography; and
4) subjecting the solution obtained at step 3) to a second cation-exchange chromatography, wherein said solution is, optionally, diluted with a buffer comprising methionine.

Briefly, the pH-adjusted, clarified protein solution containing a protein pool obtained after the oxidizing renaturation treatment is applied, in step 1), to a Phenyl-SEPHAROSE® column in order to separate renatured IFNa5 from other components, e.g., residual chaotropic agents, etc. In addition, the contact of the renatured IFNa5 with the hydrophobic surface of the adsorbent favors maturation of the IFNa5.

Then, in step 2), the protein pool obtained at step 1) is adjusted to conductivity (e.g., 13.00-14.00 mS/cm) and pH is adjusted to 8.75-8.85 and applied on a Q-SEPHAROSE® column (anion-exchange chromatography) in order to separate IFNa5 monomer from its aggregated forms. Fractions having a specific purity (e.g., equal to or higher than 55%) can be pooled for further purification.

Subsequently, in step 3), the protein pool obtained at step 2) is adjusted to conductivity (e.g., 6.00-7.00 mS/cm) and pH is adjusted to 5.15-5.20 and applied on a SP-SEPHAROSE® column (first cation-exchange chromatography) in order to separate the main IFNa5 form from charged isoforms like as N-methionyl-IFNa5 and acetylated IFNa5 (forms which are the products of post-translational modifications). Fractions having a specific purity (e.g., equal to or higher than 70%) can be pooled for further purification.

Finally, in step 4), the protein pool obtained at step 3) is adjusted to conductivity (e.g., 6.00-7.00 mS/cm) and pH is adjusted to 5.00-5.20 and applied on a second SP-SEPHAROSE® column (second cation-exchange chromatography) in order to separate the main IFNa5 form from charged isoforms. In a particular embodiment, L-methionine is added to the loading solution in order to prevent oxidation of IFNa5 during chromatography performed at room temperature. Fractions can be pooled in such a way that a purity of IFNa5 equal to or higher than ($\geq$) 95% (determined by RP-HPLC) can be achieved.

If desired, the IFNa5 so obtained may be formulated with pharmaceutically acceptable vehicles and excipients, e.g., sodium phosphate, pH 6.80-7.20, containing sodium chloride. The protein solution, if desired, can be concentrated up to the desired concentration, for example, in a particular embodiment, the protein solution is concentrated up to 10 mg/mL, e.g., up to 1.0-1.5 mg/mL protein concentration, and buffer exchanged by ultrafiltration and sterilized using sterile filtration through a sterile filter unit with maximum pore size of 0.22 p.m.

Example 3 discloses a process for isolating and purifying hIFNa5 from a hIFNa5 producing strain.

The following examples serve to further illustrate the embodiments of the present invention.

Example 1

Construction of the *E. coli* Strain Expressing IFNa5

This example discloses the development and construction of the *E. coli* strain producing recombinant human interferon alpha-5 (hIFNa5). Briefly, the cloning and expression of the hIFNa5 gene and the construction of the bacterial strain producing recombinant IFNa5 protein was achieved as described below by using the following steps: cloning of the cDNA gene encoding hIFNa5, modification of the DNA sequence of said gene to optimize its expression in *E. coli*, construction of the expression plasmid, transformation of the selected plasmid into a suitable *E. coli* strain and selection of expression/induction conditions.

Methods

Conventional methods and protocols were used in cloning and expression of hIFNa5 [Sambrook et al. Molecular cloning: A Laboratory Manual. Second ed., CSH Laboratory, Cold Spring Harbor, 1989; Current Protocols in Molecular Biology, vol. 1-3 (Ausubel F. M. et al., ed.) John Wiley & Sons, Inc., Brooklyn, N.Y., 1994-1998].

All operations with enzymes, DNA and protein markers were performed according to the manufacturer instructions [mainly Fermentas (Lithuania)].

Genetic Construction

The construction of the hIFNa5 producing *E. coli* was performed following the steps shown in the flowchart of the development of the genetic constructions depicted in FIG. 1.

Primary Plasmid

The hIFNa5 coding sequence (without signal peptide) was cloned from normal liver tissue from an anonymous donor patient—after informed consent—undergoing abdominal surgery from a non-liver pathology as follows: Normal liver tissue was homogenized in 1 mL of Ultraspec solution (Biotex) and total RNA was treated with Dnase (Gibco-BRL, Paisley, U.K.) prior to reverse transcription with M-MLV Reverse Transcriptase (Gibco-BRL) in presence of Rnase-OUT (Gibco-BRL). hIFNa5 coding sequence (without signal peptide) was PCR amplified from the complementary DNA (cDNA) previously obtained, using the following upstream and downstream primers (5'-3'):

```
                                         (SEQ ID NO: 2)
       GGAATTCCATATGTGTGATCTGCCTCAGACCCA,
       and (SEQ ID NO: 3)
       CGGGATCCTTGAACCAGTTTTCATTCCTTC.
```

Both primers contain hIFNa5 sequence (in bold) and specific sequences to the restriction enzymes: NdeI and BamHI (underlined) The PCR product was analyzed by agarose gel electrophoresis and the band was excised from the gel and purified by Gene Clean kit (MP Biomedicals). The purified PCR product was cloned in the pCR 2.1 TOPO plasmid using the TOPO TA Cloning Kit (Invitogen). Clones from the insert were sequenced in ABI PRISM 310 Genetic Analyzer (Perkin Elmer) using the dye Rhodamine terminator cycle sequencing kit (Perkin Elmer) to verify that the insert correspond exactly with the hIFNa5 sequence. After that, pCR 2.1 TOPO-IFNalpha5 was digested with NdeI and BamHI restriction enzymes, and the 534 pb band (corresponding to IFNa5 coding sequence) was cloned in the pET28b vector (Novagen) previously digested with the same enzymes. The sequence was again verified by using the same procedure.

Primary plasmid DNA pET28-IFN alpha-5 from different colonies was analysed by restriction analysis (FIG. 2).

Plasmid pET28-IFN alpha-5 was analyzed by sequencing both DNA strands using an ABI Prism 377 sequence analyzer. This analysis confirmed the hIFNa5 coding sequence. Plasmid pET28-IFN alpha-5 was used for the construction of the mature structure with codon optimization as a template for PCR amplification.

Mature Structure with Codon Optimisation

PCR Amplification of hIFNa5 Coding Gene Including Codon Optimization

PCR amplification was performed by using plasmid pET28-IFN alpha-5 as template. The following oligonucleotides were synthesized:

```
Sense primer (SP):
                                         [SEQ ID NO: 4]
5'- CAT ATG TGT GAT CTG CCG CAG ACC CAC TCC

CTG TCT AAC CGT CGT ACT CTG ATG ATC ATG GCA

CAG ATG GGT CGT ATC TCT CCT TTC

Antisense primer (ASP):
                                         [SEQ ID NO: 5]
5'- CTG CAG TTA TTC CTT ACG ACG TAA ACG

TTC TTG CAA G
```

SP [SEQ ID NO: 4] and ASP [SEQ ID NO: 5] primers have been applied to substitute the codons which are the least frequently used in *E. coli*. Codon optimization mainly concerns arginine codons AGA and AGG.

Cloning of PCR Fragment into Intermediate Plasmid

Figure 3:
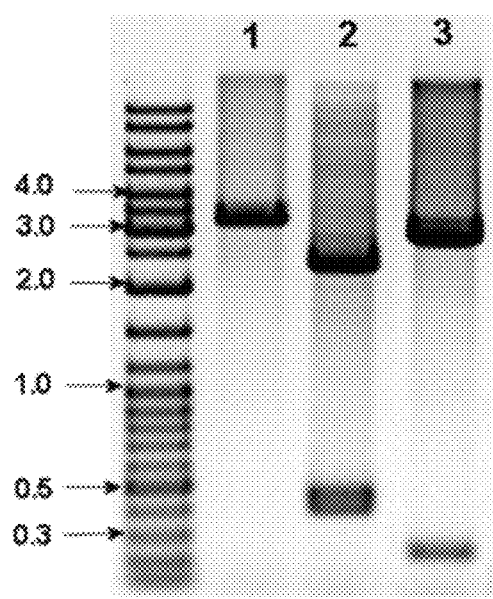
FIG. 3 shows the results of the restriction analysis of intermediate plasmid IFN alpha-5. The plasmid was derived from a single clone. Size of marker DNA (Gene Ruler DNA Ladder Mix, Fermentas, Lithuania) bands in kbp is indicated. Expected fragment sizes (in bp) are given in parentheses. Lane 1: pUC57-IFN alpha-5/PstI (28; 3197); lane 2: pUC57-IFN alpha-5/PvuII (455; 406; 2364); lane 3: pUC57-IFN alpha-5/NdeI (250; 2975).

The purified amplification products of approx. 500 bp cloned into pUC57/T plasmid (#SD0171 Fermentas, Lithuania) using Rapid DNA ligation Kit (#K1421, Fermentas, Lithuania) and transformed into *E. coli* JM109 (ATCC 53323, ATCC Bacteria and Bacteriophages, 19$^{th}$ edition, 1996). Recombinant clones were selected by restriction analysis (FIG. 3). Two clones were selected and the extracted plasmids were sequenced.

Sequence Analysis of Intermediate Plasmid IFN Alpha-5 and Recloning of Human IFN Alpha-5 Coding Sequence into Plasmid pET21b (+)

The nucleotide sequence analysis confirmed the sequence of hIFNa5 coding portion and is shown in FIG. 4.

Figure 5:
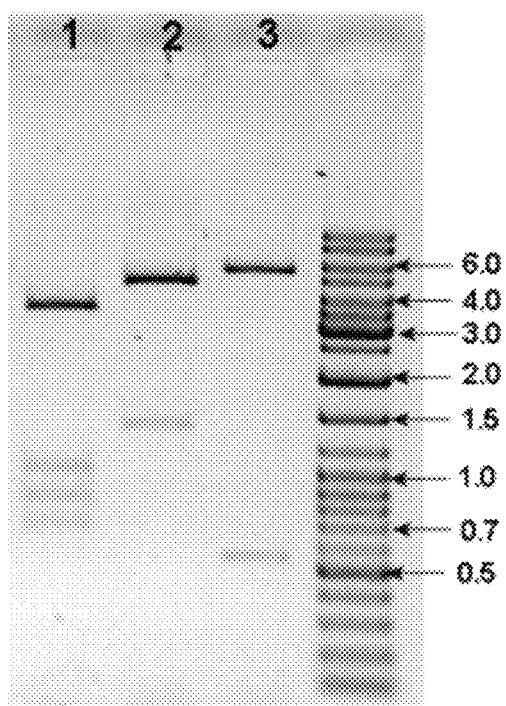
FIG. 5 shows the results of the restriction analysis of plasmid pET21-IFN alpha-5. The plasmid was derived from a single clone. Size of marker DNA (Gene Ruler DNA Ladder Mix, Fermentas, Lithuania) bands in kbp is indicated. Expected fragment sizes (in bps) are given in parentheses. Lane 1: pET21-IFN alpha-5/PagI (673; 817; 1008; 3423); lane 2: pET21-IFN alpha-5/PstI (1352; 4569); lane 3: pET21-IFN alpha-5/NdeI+BamHI (516; 5405).

The hIFNa5 coding fragment was NdeI+BamHI cut out and the purified DNA fragment was ligated into NdeI+BamHI cut vector pET21b(+) (Novagen) to render the plasmid pET21-IFN alpha-5. After transformation into *E. coli* JM109 strain, bacteria were selected by adding 100 μg/mL of ampicillin. Recombinant insert analysis of colonies resulting from transformed cells was performed using colony PCR testing method. Detailed restriction analysis of plasmid pET21-IFN alpha-5, purified from PCR positive clones, resulted in the expected restriction pattern (FIG. 5).

Expression of Recombinant hIFNa5

Figure 6:
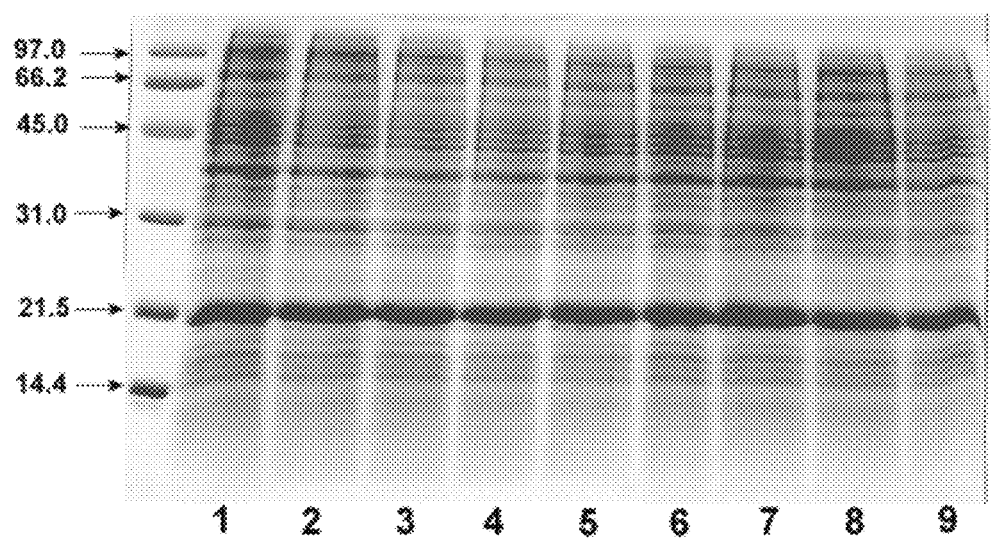
FIG. 6 shows the expression of recombinant IFNa5 protein. The cell culture *E. coli* BL21(DE3) pET21-IFN alpha-5 picked from 9 colonies (lanes 1-9) were grown in 750 mL flasks (LB medium, volume 250 mL) at 37° C. to OD$_{600}$ of about 1.2. Target protein expression induced with 1 mM IPTG for 2.5 hours. Total cell protein samples were run along with BioRad Protein Markers (in kDa indicated on the left) on 15% SDS-PAGE followed by staining with Coomassie blue.

After the plasmid pET21-IFN alpha-5 was established (stabilized) in a non-expressing host, it was transformed into a host *E. coli* BL21(DE3) bearing relevant genetic elements for expression of target proteins to render the *E. coli* BL21 (DE3) pET21-IFN a-5 strain. The hIFNa5 expression was induced with 1 mM IPTG (isopropyl-β-D-thiogalactopyranoside) and the results are shown in FIG. 6.

According to SDS-PAGE molecular weight of hIFNa5 is about 20 kDa, which correlates with calculated 19.7 kDa.

The recombinant hIFNa5 was detected in the insoluble fraction of the total cell lysate; the target protein yield was about 20% of the total cell protein. The hIFNa5 comprised nearly 40% of the insoluble fraction of the cell lysate. One colony of the expression strain obtained was used for the establishment of the research master cell bank (RMCB).

Example 2

Biosynthesis Process of hIFNa5 by a Producing Strain

The *E. coli* BL21 (DE3) pET21-IFN a-5 strain (Example 1) was cultivated in a media having the following composition (g/L):
- a) for inoculum preparation (cultivation) in the flasks (g/L): di-sodium hydrogen phosphate (17.0), potassium dihydrogen phosphate (1.82), ammonium sulfate (3.0), magnesium sulfate heptahydrate (0.5), D(+)-glucose monohydrate (15.0) and microelements stock solution e) (0.16 mL);
- b) for fermentation (g/L): ammonium phosphate dibasic (4.0), magnesium sulfate heptahydrate (0.5), potassium dihydrogen phosphate (13.3), citric acid monohydrate (1.6), D(+)-glucose monohydrate (30.0) and microelements stock solution e) (0.25 mL);
- c) feeding solution A (g/L): D(+)-glucose monohydrate (700.0), magnesium sulfate heptahydrate (20.7) and microelements stock solution e) (3.4 mL/L);
- d) feeding solution B (g/L): ammonium phosphate dibasic (360.0) and potassium dihydrogen phosphate (306.7); and
- e) microelements (trace elements) stock solution (g/L): iron (III) chloride hexahydrate (30.0), calcium chloride dihydrate (4.05), zinc (II) sulfate heptahydrate (6.75), manganese (II) sulfate monohydrate (1.5), copper (II) sulfate pentahydrate (3.0), cobalt (II) chloride hexahydrate (1.14), sodium molybdate dihydrate (0.3) and boric acid (0.69).

Figure 7:
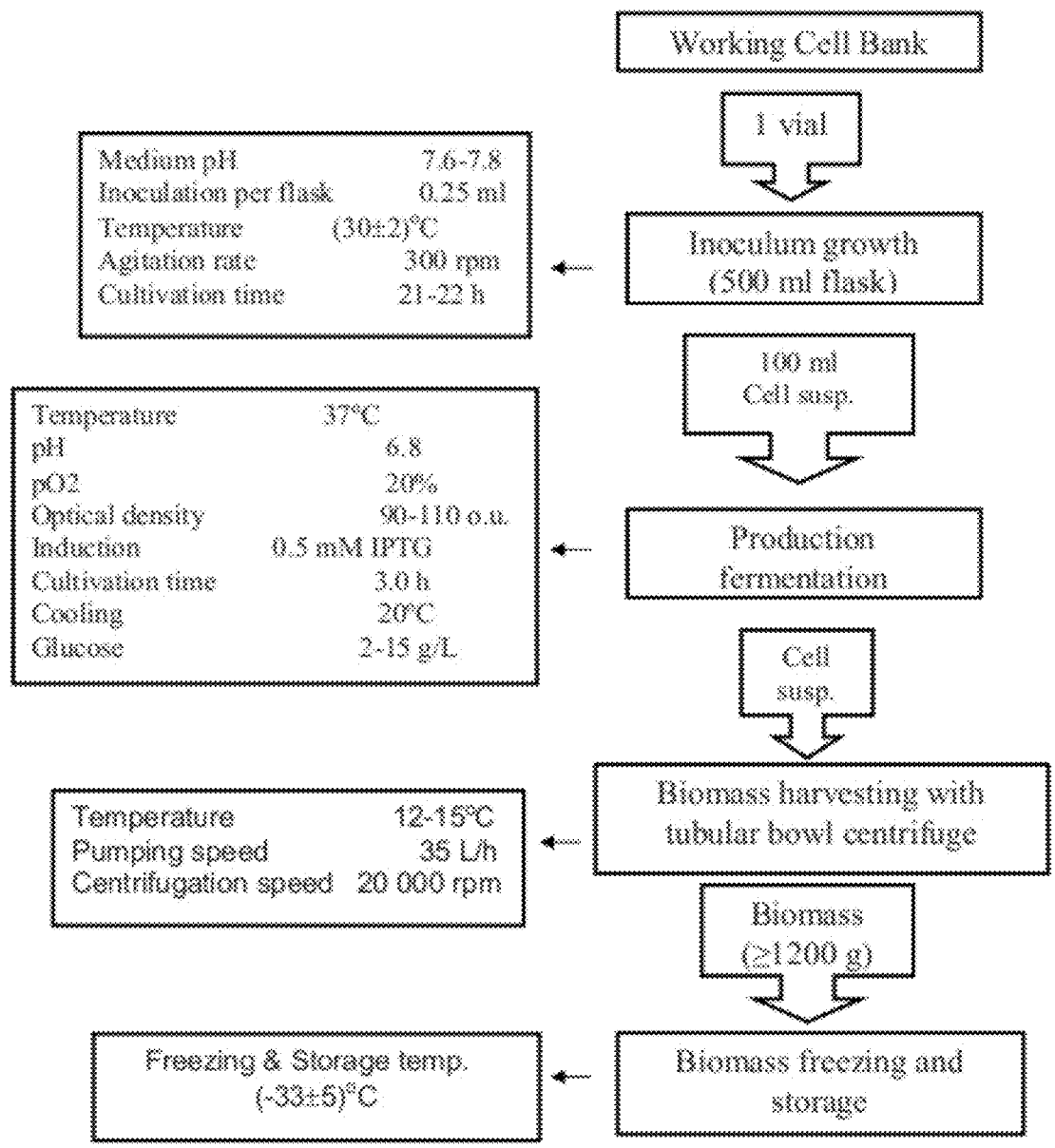
FIG. 7 shows the flow chart of the biosynthesis of recombinant hIFNa5.

FIG. 7 shows the full scheme of the human IFN alpha-5 biosynthesis process.

Inoculum Preparation:

An Erlenmeyer flask, containing 500 mL of sterile medium for cultivation in the flasks [a)], was inoculated with 0.25 mL of stock culture WCB (working cell bank) *E. coli* BL21 (DE3) pET21-IFN a-5. Thereafter, the flask was incubated in a rotating shaker with agitation speed 300 rpm, at 30° C. temperature for 21-22 hours. Optical density after incubation must be equal to or higher than 4.50 o.u. (optical units) [λ=595 nm].

Fermentation:

A fermentor (13.7 L total volume) containing 7.0 L of fermentation medium [b)] was inoculated with 1.5-1.6% of the culture obtained in the inoculum flask. Fermentation was performed at automatically controlled temperature (37° C.), pH (6.8) and $pO_2$ (20%). 25% ammonium solution was used for pH correction. After 8-9 hours cultivation, additional feeding was started. Feeding solution A [c)] was pumped in certain doses in order to keep the concentration of glucose in the cultivation medium between about 3 g/L and 22 g/L. Induction was performed with IPTG at 90-110 o.u. (λ=595 nm) to make final IPTG concentration of 0.5 mM. Specific culture growth rate at induction point should not be lower than 0.45 in order to have sufficient specific growth rate after induction. Average specific culture growth rate after induction should be higher than 0.17. Feeding solution B [d)] was pumped in separate doses: 150 mL at 60-70 o.u., 150 mL at 120-140 o.u., 75 mL at 1.5 hours (90 minutes) and 75 mL at 2 hours after induction. Fermentation was continued for 3 hours after induction at the same conditions. Then the cell suspension was cooled down in the fermentor at 12-15° C. and transferred into a centrifuge by a peristaltic pump (35 L/h). The cell suspension was centrifuged at 5,000 rpm speed at 4° C.

The harvested biomass was collected into a polyethylene bag and placed into (−33±5)° C. refrigerator for freezing and subsequent storage. A portion of frozen biomass was taken for evaluation of total proteins and expression of hIFNa5.

Example 3

Process for Isolating and Purifying hIFNa5 from a Producing Strain

1. Biomass Homogenization, Disruption and Isolation of Inclusion Bodies (IBs)

680.0-700.0 g of the biomass obtained in Example 2 was homogenized in a resuspension buffer (0.1 M Tris-HCl, pH 7.80-8.00, containing 2 mM EDTA, 0.1% TritonX-100 and 1 mM PMSF) at a 1/10 (w/v) ratio, i.e., 1 g of wet biomass/10 mL of resuspension buffer.

Resuspension was performed in a Poter's homogenizer (Teflon/glass) and then cells were disrupted with a high pressure homogenizer at 600-800 bar at 4-10° C. temperature. After cells desintegration, inclusion bodies (IBs) were separated by centrifugation at 8,000 rpm over 30-35 min.

2. Washing of Inclusion Bodies (IBs)

Pre-washing of isolated IBs was performed by a four consecutive-step process with washing buffers I-III:

Washing buffer I: 10 mM Tris-HCl buffer, pH 7.45-7.55, containing 1 M NaCl, 0.1% Polysorbate—80;

Washing buffer II: 10 mM Tris-HCl buffer, pH 8.00-8.20, containing 6 M urea;

Washing buffer III: 10 mM Tris-HCl buffer, pH 8.00-8.20.

Briefly, washing of IBs was performed as follows:
- a) the first two washings (steps 1 and 2), the IBs were washed with washing buffer I;
- b) the third washing (step 3), the IBs were washed with washing buffer II; and
- c) the fourth washing (step 4), the IBs were washed with washing buffer III.

The washing buffer/wet biomass ratio of 10 mL of buffer/1 g wet biomass was maintained throughout the entire IBs washing procedure.

3. Solubilization of IBs

In order to solubilize the IBs, a solubilization buffer (50 mM glycine/NaOH buffer, pH 9.55-9.65, containing 6 M GdmHCl) was used. Solubilization ratio: IBs isolated from 1 g biomass in 6 mL of solubilization buffer for 2 h at 2-8° C., and following centrifugation at 8,000 rpm over 25-30 min.

4. Renaturation

Renaturation Buffer:

50 mM glycine/NaOH buffer, pH 9.55-9.65, containing 1.2 M NaCl, 0.22 M L-arginine, 2.85 mM GSH, 0.285 mM GSSG, conductivity 110-110 mS/cm at 4-10° C.

GdmHCl-denatured human IFN alpha 5 was renatured by dropwise addition of the IBs solubilisate to renaturation buffer (volume ratio 1:7) to achieve a final concentration in the renaturation mixture of 0.2 M L-arginine, 2.5/0.25 mM GSH/GSSG. Renaturation mixture was continuously stirred for 44-66 h at 2-8° C. After renaturation, the protein solution was clarified by centrifugation at 8,000 rpm over 30-35 min.

5. Chromatography hIFNa5 was purified by a four-step chromatographic process as mentioned below.

5.1 Chromatography Over a Phenyl-SEPHAROSE® Column (Hydrophobic Interaction Chromatography)

The Phenyl-SEPHAROSE® column is intended for separating renatured hIFNa5 from residual chaotropic agent GdmHCl. In addition, the contact of renatured hIFNa5 with the hydrophobic surface of the adsorbent favors maturation of hIFNa5.

Briefly, the pH of the clarified protein solution was adjusted to 8.00-8.20 with 6 M HCl and the protein solution was then applied on a chromatography Phenyl-SEPHAROSE® column with the following process parameters:

Chromatography medium: Phenyl-SEPHAROSE® Fast Flow (Amersham Pharmacia Biotech AB);

Column used: BPG 100×500 mm, diameter 10 cm;

Linear flow rate: 60 cm/hour;

Chromatography medium bed volume: 2.7.+-.0.3 L

Equilibration buffer: 20 mM Tris-HCl buffer, pH 8.00-8.20, containing 1.5 M sodium chloride, conductivity 115-125 mS/cm at 15-25.degree. C. (110-120 mS/cm at 4-10° C.);

Elution buffer: 10 mM Tris-HCl buffer, pH 9.20-9.25, conductivity 0.1-0.2 mS/cm at 15-25°. C;

Elution over 6 column volumes (CV) [i.e., 6 CV] with elution buffer is performed. Collected protein solution 2-6 CV.

5.2 Chromatography Over a Q-SEPHAROSE® Column (Anion-Exchange Chromatography)

The Q-SEPHAROSE® column is used for separating hIFNa5 monomer from its aggregated forms.

Briefly, the protein pool obtained at the preceding step (5.1) was adjusted to conductivity of 13.00-14.00 mS/cm by adding 20 mM Tris-HCl buffer, pH 8.75-8.85, containing 5 M NaCl, and pH was adjusted to 8.75-8.85 with 6 M HCl. The protein solution was then applied onto a chromatography Q-SEPHAROSE® column with the following process parameters:

Chromatography medium: Q-SEPHAROSE® Fast Flow (Amersham Pharmacia Biotech AB);

Column used: BPG 140×500 mM, diameter 14 cm;

Linear flow rate: 60 cm/hour;

Chromatography medium bed volume: 3.3.+-.0.3 L

Equilibration buffer: 20 mM Tris-HCl buffer, pH 8.75-8.85, containing 0.12 M sodium chloride, conductivity 13.00-14.00 mS/cm at 15-25° C.;

Elution buffer: 20 mM Tris-HCl buffer, pH 8.75-8.85, containing 0.23 mM sodium chloride, conductivity 23.00-25.00 mS/cm at 15-25° C.;

Elution: linear gradient to 100% elution buffer over 5 column volumes (5 CV) and 5 CV 100% elution buffer.

Fraction volume was 400-1,000 mL.

Only fractions of equal to or higher than (≥) 55% purity of hIFNa5 (as determined by RP-HPLC) were pooled for further purification.

5.3 First Chromatography Over a SP-SEPHAROSE® Column (Cation-Exchange Chromatography I)

The SP-SEPHAROSE® column is used for the third and fourth chromatography steps in order to separate the main hIFNa5 form from charged isoforms like as N-methionyl-hIFNa5 and acetylated hIFNa5 (forms which are the products of post-translational modifications).

Briefly, the protein pool obtained at the preceding step (5.2) was adjusted to conductivity of 6.00-7.00 mS/cm by adding 10 mM sodium acetate buffer, pH4.95-5.05, and pH was adjusted to 5.15-5.20 with 4 M acetic acid. The protein solution was then applied onto a chromatography SP-SEPHAROSE® column with the following process parameters:

Chromatography medium: SP-SEPHAROSE® Fast Flow (Amersham Pharmacia Biotech AB);

Column used: BPG 100×500 mm, diameter 10 cm;

Linear flow rate: 60 cm/hour; [0162] Chromatography medium bed volume: 3.3.+-.0.3 L Equilibration buffer: 20 mM sodium acetate buffer, pH 5.15-5.20, containing 50 mM sodium chloride, conductivity 6.00-7.00 mS/cm at 15-25° C.;

Elution buffer: 20 mM sodium acetate buffer, pH 5.15-5.20, containing 2 mM L-methionine and 0.1 M NaCl, conductivity 11.00-13.00 mS/cm at 15-25° C.; Elution over 10 column volumes (10 CV) with elution buffer was performed.

Fraction volume was 400-2,000 mL.

Only fractions of equal to or higher than (≥) 70% purity of hIFNa5 (as determined by RP-HPLC) were pooled for further purification.

5.4 Second Chromatography Over a SP-SEPHAROSE® Column (Cation-Exchange Chromatography II)

Briefly, the loading solution [pool of protein fraction recovered from the first SP-SEPHAROSE® column (step 5.3)] was diluted with 5 mM sodium acetate buffer, pH 5.00-5.20, containing 2 mM L-methionine, conductivity of 0.200-0.800 mS/cm at 15-25° C. to conductivity of 6.00-7.00 mS/cm at 15-25° C. Inclusion of 2 mM L-methionine into the loading solution was done in order to prevent oxidation of hIFNa5 during chromatography performed at room temperature. The loading solution was applied on a chromatography SP-SEPHAROSE® column with the following process parameters:

Chromatography medium: SP-SEPHAROSE® Fast Flow (Amersham Pharmacia Biotech AB);

Column used: BPG 100×500 mm, diameter 10 cm;

Linear flow rate: 60 cm/hour;

Chromatography medium bed volume: 3.0.+-.0.3 L

Equilibration buffer: 20 mM sodium acetate buffer, pH 5.15-5.20, containing 50 mM sodium chloride, conductivity 6.00-7.00 mS/cm at 15-25° C.;

Elution buffer: 20 mM sodium acetate buffer, pH 5.15-5.20, containing 0.1 M NaCl, conductivity 11.00-13.00 mS/cm at 15-25° C.;

Elution linear flow rate: 45 cm/hour;

Elution: linear gradient to 100% elution buffer over 20 column volumes (20 CV).

Fraction volume was 400-2,000 mL.

Fractions were pooled in such a way that RP-HPLC purity of hIFNa5 is equal to or higher than (≥) 95%.

Formulation, Concentration, Sterile Filtration

Formulation Buffer:

25 mM sodium phosphate, pH 6.80-7.20, containing 0.1 M sodium chloride, conductivity 10.00-14.00 mS/cm at 15-25° C.

The buffer exchange/concentration of protein solution was performed by diafiltration/concentration through Biomax 10 kDa membrane equal to or higher than (≥) 1.00 mg/mL, sterile filtered through a sterile 0.22 µm filter (Millipak 20) and filled into glass vials.

Figure 8A:
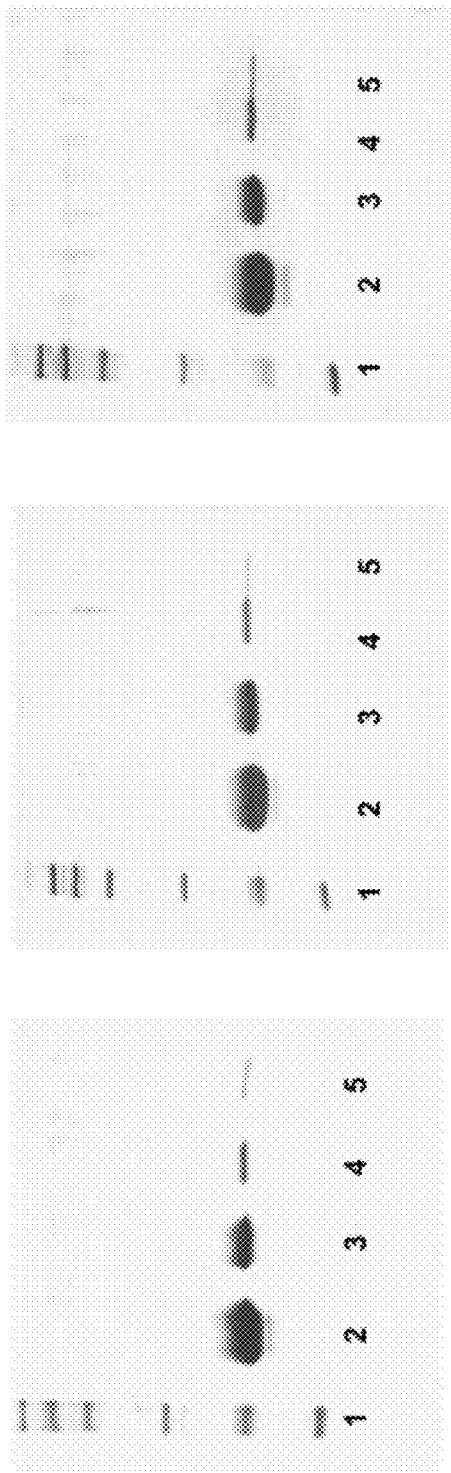
FIG. 8 represents the purity of recombinant hIFNa5 processed and formulated according to this invention as determined by SDS-PAGE (14%) under both reducing (FIG. 8A) and non-reducing (FIG. 8B) conditions of hIFNa5 protein (the figure shows the results of three large-scale purification batches of hIFNa5 protein).
Figure 8D:
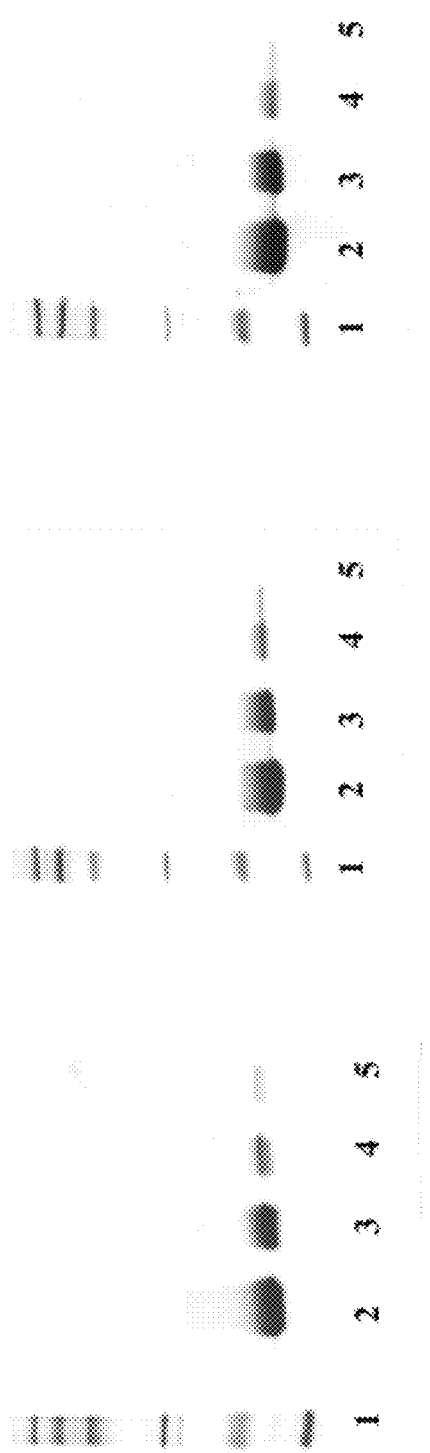

FIG. 8 shows the purity of the recombinant hIFNa5 processed and formulated according to this invention as determined by SDS-PAGE (14%) under both reducing and non-reducing conditions of recombinant hIFNa5 protein of three large-scale purification batches.

Figure 9:
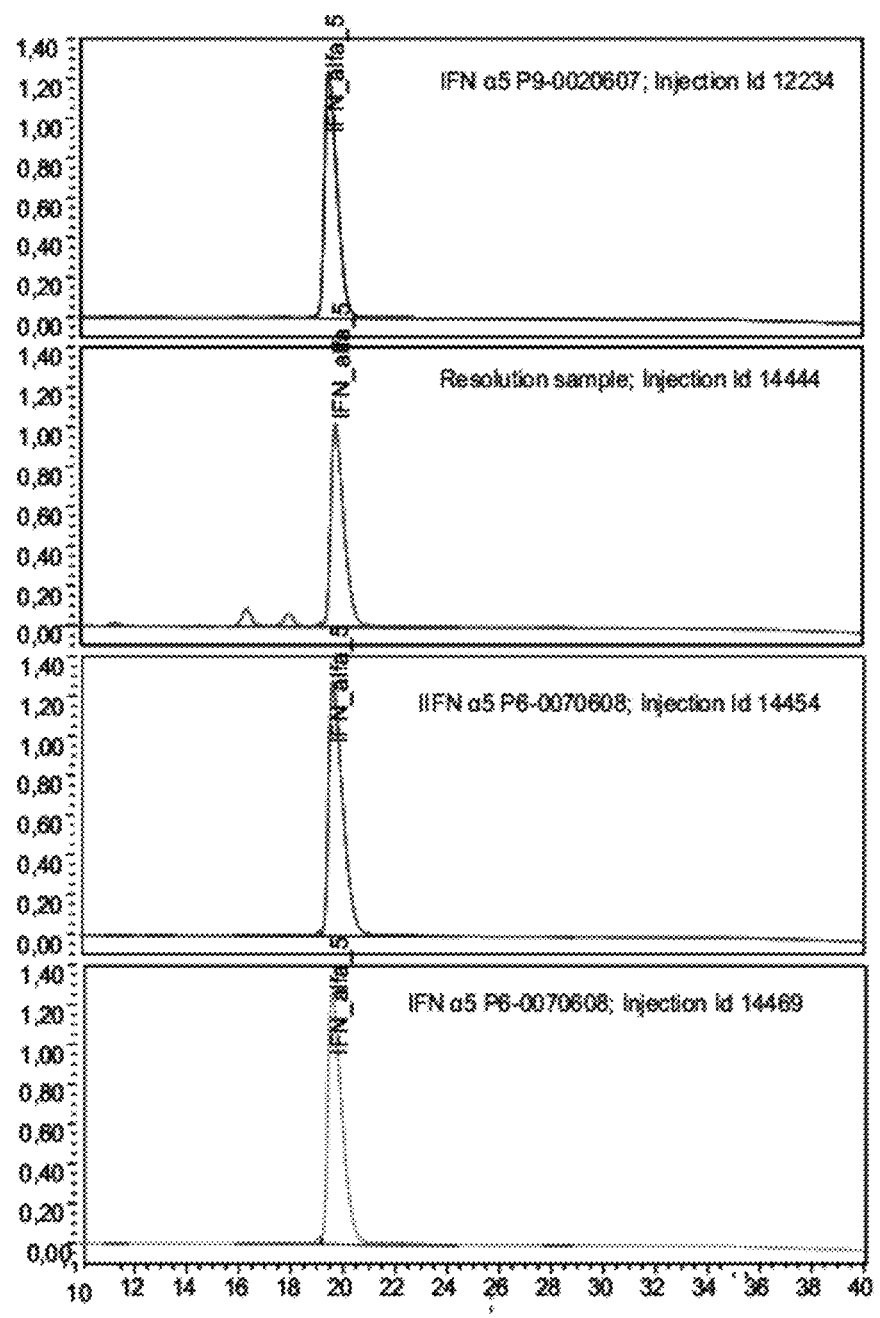
FIG. 9 shows the purity of the recombinant hIFNa5 processed and formulated according to this invention as determined by "reversed phase—high performance liquid chromatography" (RP-HPLC) analysis (the figure shows the results of three large-scale batches of recombinant hIFNa5).

FIG. 9 shows the purity of the recombinant hIFNa5 processed and formulated according to this invention as determined by "reversed phase—high performance liquid chromatography" (RP-HPLC) analysis (the figures shows the results of three large-scale batches of recombinant hIFNa5).

Figure 10:
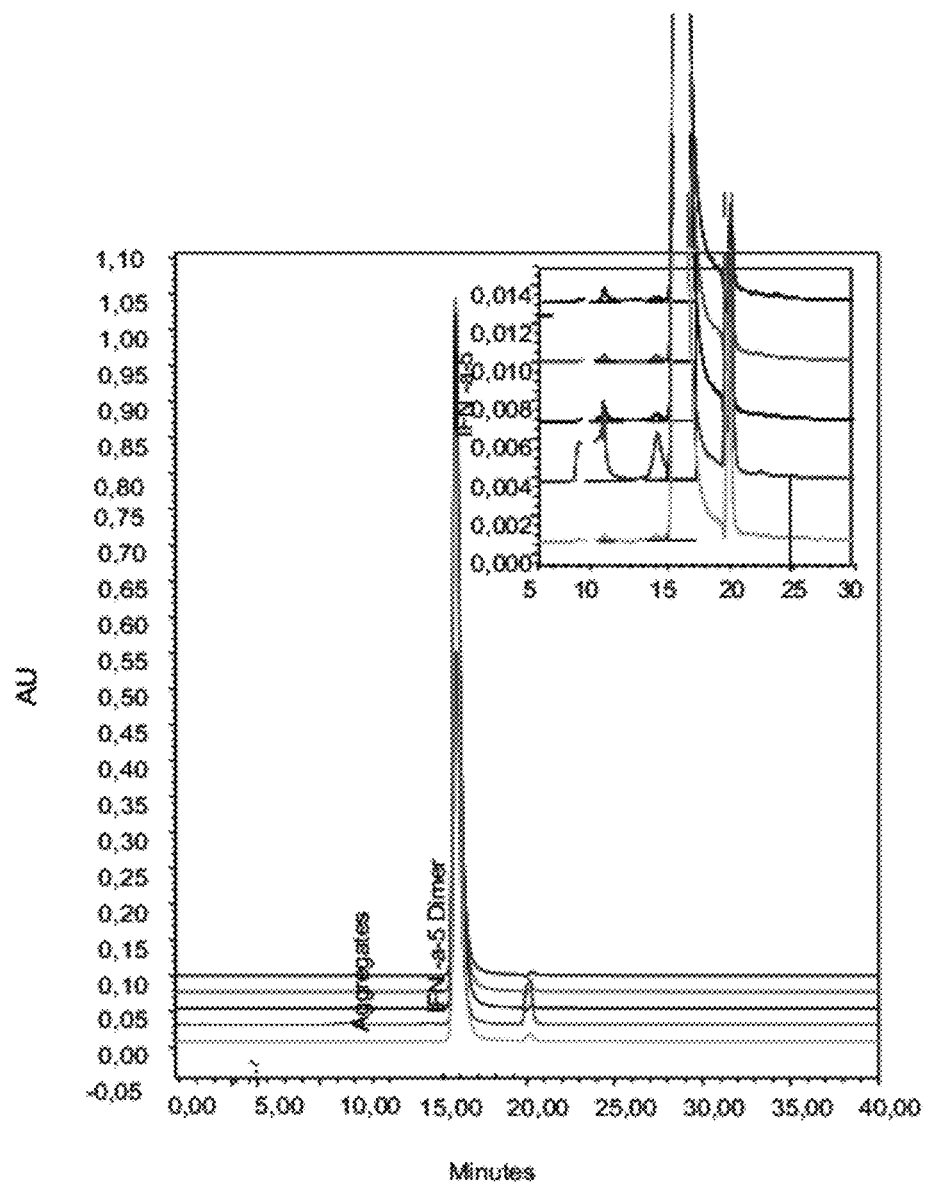
FIG. 10 shows the purity of the recombinant hIFNa5 processed and formulated according to this invention as determined by "size exclusion—HPLC" (SE-HPLC) analyses (the figure shows the results of three large-scale batches of recombinant hIFNa5).

FIG. 10 shows the purity of the recombinant hIFNa5 processed and formulated according to this invention as determined by "size exclusion—HPLC" (SE-HPLC) analyses for three recombinant hIFNa5 large scale batches.

Figure 11:
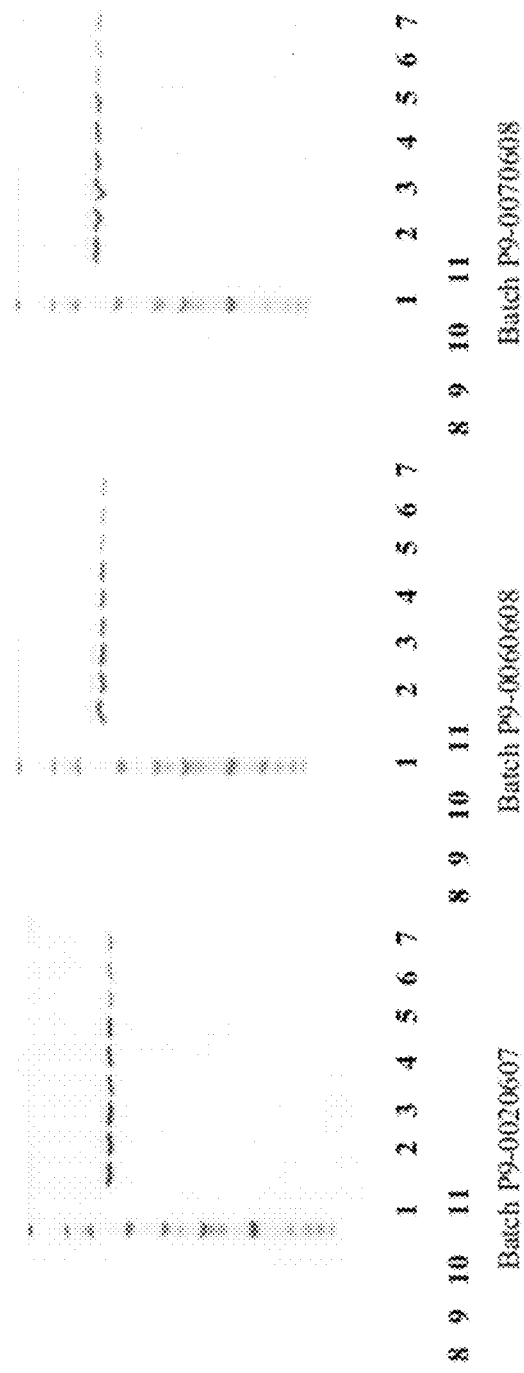
FIG. 11 shows the purity of recombinant hIFNa5 processed and formulated according to this invention as determined by isoelectric focusing analyses (the figure shows the results of three large-scale batches of recombinant hIFNa5). Lanes 1, 11: pI standards (Amersham Pharmacia); lanes 2, 3, 4: recombinant hIFNa5, 15 µg; lanes 5, 6, 7: recombinant hIFNa5, 5 µg; lanes 8, 9, 10: recombinant hIFNa5, 1 µg.

FIG. 11 shows the purity of recombinant hIFNa5 processed and formulated according to this invention as determined by isoelectric focusing analyses for three recombinant hIFNa5 large scale batches. Lanes 1, 11: pI standards (Amersham Pharmacia); lanes 2, 3, 4: recombinant hIFNa5, 15 µg; lanes 5, 6, 7: recombinant hIFNa5, 5 µg; lanes 8, 9, 10: recombinant hIFNa5, 1 µg.

Figure 12:
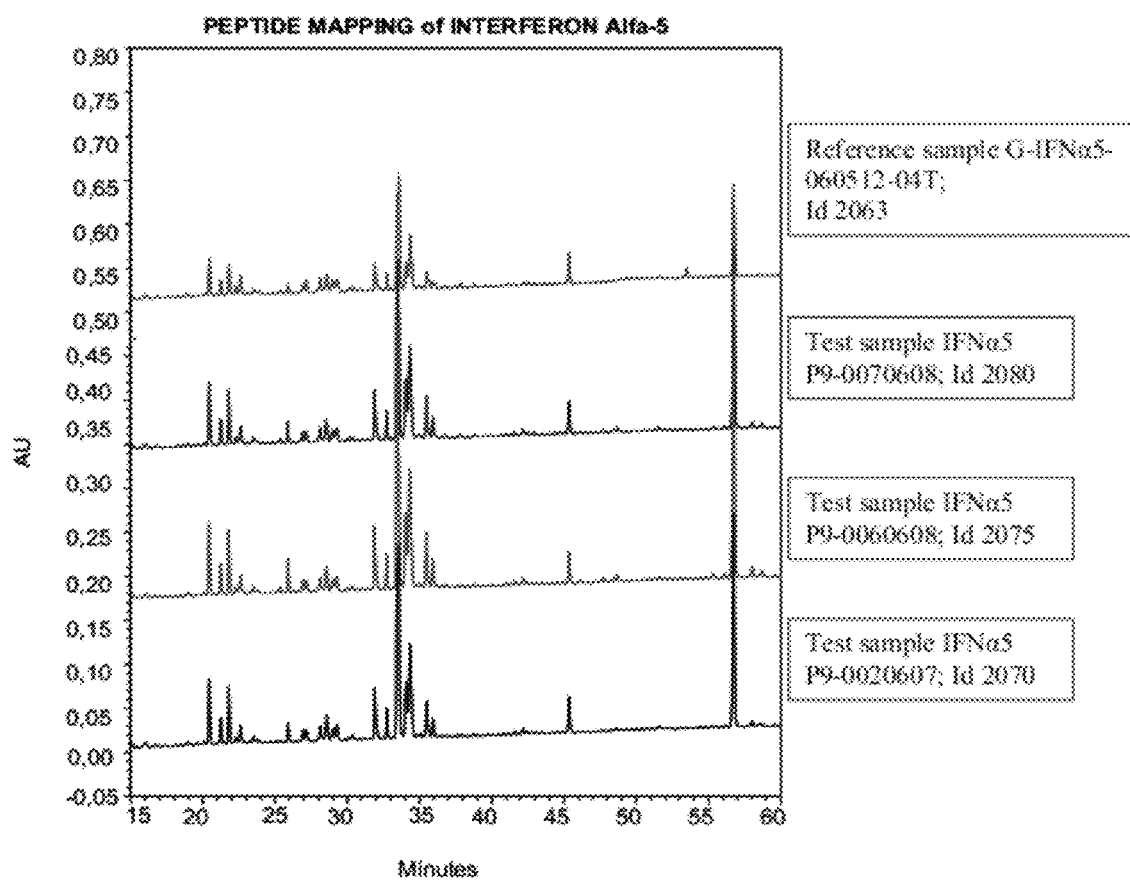
FIG. 12 shows the peptide mapping chromatograms of three recombinant hIFNa5 preparations large-scale batches purified and formulated according to this invention.

FIG. 12 represents the peptide mapping chromatograms of three recombinant hIFNa5 preparations large-scale batches purified and formulated according to this invention.

Example 4

Evaluation of Microelements and Glucose Concentration Effect on Biosynthesis of Recombinant Human IFN Alfa-5

The purpose of this example was to confirm the effect of microelements on post-translational modifications of recombinant human IFN alfa-5 (hIFNa5), to determine the limits of critical microelements concentration in the carbon feed solution and to evaluate the effect of glucose concentration on the biosynthesis of recombinant hIFNa5. Thus, this example describes the analysis performed and the results obtained during the study and serves as justification of microelements concentration in the carbon feed solution and justification of glucose concentration in the biosynthesis process of recombinant hIFNa5.

During the optimization of the hIFNa5 biosynthesis process, it was detected that the concentration of metals or microelements (trace elements) in the fermentation medium had an effect on the post-translational modifications of hIFNa5 protein. Thus, the purpose of this study was to confirm the effect of said trace elements on post-translational modifications of hIFNa5 protein and to determine the limits of the critical microelements concentration in the carbon feed solution. In addition to that, it was decided to evaluate glucose concentration (17 g/L and 22 g/L) in the fermentation medium after supply of each carbon feed dose in order to learn if it has any effect on the culture growth (i.e., if it involves a culture growth limitation thus affecting to the biomass yield or if it has no effect on the culture growth) as well as on the quality of the target protein (recombinant hIFNa5).

Materials and Methods

The plan of experiments was designed and monitored with the help of "Design of Experiments" (DOE) and it is shown in Table 1.

TABLE 1

| | Designed and performed experiments | |
|---|---|---|
| Short batch No. | Concentration of microelements solution in the carbon feed solution, mL/L | Upper limit of glucose concentration in the fermentation medium, g/L |
| M-83 | 2.2 | 17 |
| M-84 | 2.2 | 22 |
| M-85 | 2.7 | 17 |
| M-86 | 2.7 | 22 |
| M-87 | 3.7 | 17 |
| M-88 | 3.7 | 22 |
| M-89 | 4.2 | 17 |
| M-90 | 4.2 | 22 |
| M-92 | 3.2 | 22 |
| M-80*; M-81* | 3.0 | 22 |
| M-82* | 3.4 | 22 |
| F-0030811* | 4.0 | 22 |

Included experiments (*) which had been previously performed under the same conditions earlier.

High cell density fed-batch fermentations were performed in a chemically defined mineral salt/glucose medium.

Composition of mineral salt/glucose medium for cultivation in the flask (g/L): di-sodium hydrogen phosphate—17.0, potassium dihydrogen phosphate—1.82, ammonium sulphate—3.0, magnesium sulfate heptahydrate—0.5, D(+)-glucose monohidrate—15.0, microelements stock solution—0.16 mL.

Microelements (trace elements or metals) stock solution (g/L): iron (III) chloride hexahydrate—30.0, calcium chloride dihydrate—4.05, zinc (II) sulfate heptahydrate—6.75, manganese (II) sulfate monohydrate—1.5, copper (II) sulfate pentahydrate—3.0, cobalt (II) chloride hexahydrate—1.14, sodium molybdate dihydrate—0.3, boric acid—0.69.

Composition of mineral salt/glucose medium for fermentation (g/L): ammonium phosphate dibasic—4.0, magnesium sulfate heptahydrate—0.5, potassium dihydrogen phosphate—13.3, citric acid monohydrate—1.6, D(+)-Glucose monohidrate—30.0, microelements stock solution—0.25 mL.

Carbon feed solution: 70.0% glucose, 2.1% $MgSO_4 \times 7H_2O$ and microelements stock solution according to the experiment plan.

Glucose concentration starting from the $8^{th}$ cultivation hour was measured every (15-30) min and after that a calculated (to reach the upper glucose concentration limit of 17 g/L or 22 g/L according to the experiment plan) dose of carbon feed was added.

In addition, 70 mL of both phosphates solution (ammonium phosphate dibasic—25.0 g, potassium dihydrogen phosphate—21.0 g divided into 3 doses:ratio 2:2:1 or 28:28:14 mL) in separate doses were added at 60-75, 120-135 and 170-180 o.u.

If necessary, incoming air was automatically enriched with pure oxygen (up to 60% per liter of total fermentor volume) to maintain dissolved oxygen concentration at 20%.

0.25 mL of stock culture *E. coli* BL21 (DE3) pET21-IFN a-5 from WCB (stored at −70° C.) [Example 2] was multiplied in 500 mL of the mineral salt/glucose medium (pH about 7.7) incubated in an orbital shaker (300 rpm) for 22 hours at 30° C.

The inoculum were about 1.0% (20 mL) of the working fermentor volume what is 1.54% of the real volume.

Fermentations were performed in 3 L total/2 L working volume fermentor "Biostat B" at pH 6.8, $pO_2$—20%, temperature—37° C. Automatically controlled fermentation process on-line variables (temperature, stirring, pH, $pO_2$, acid/base consumption) and off-line variable—optical density traced in MFCS/win plots.

35% orto-phosphoric acid and 25% ammonia solution was used for pH correction.

Foam was extinguished with 20% Pluronic® 31R1.

Induction was performed at an OD of 91.6-103.6 o.u. ($\lambda$=600 nm) with IPTG to make final IPTG concentration of 0.5 mM for final working volume. Fermentation continued for other 3 hours.

Specific culture growth rate ($\mu$), incoming (additional feeding) and out coming (sampling for measurement of OD and glucose) volumes were strictly calculated all over fermentations.

Results and Data Analysis

The analysis performed and the results obtained during this study ensure that post-translational modifications of recombinant hIFNa5 protein produced in *E. coli* depend on the concentration of the microelements in the cultivation medium.

The oxidized methionilated hIFNa5 related protein was eliminated when the concentration of microelements (stock solution) was equal to or higher than 3.0 mL/L carbon feed solution or equal to or higher than 0.95 mL/L real final suspension volume and the average specific culture growth rate ($\mu$) after induction was equal to or higher than ($\geq$) 0.17 (Tables 2-3).

TABLE 2

Biosynthesis parameters at different concentration of microelements in carbon feed solution

| | | Micro-elements | | Fermentation | | | | | | hIFNa5 |
| | | | | Time elapsed | OD (600 nm) | | | | | |
| Short batch No. | Flask OD (600 nm) | stock sol. (mL/L carbon feed) | Upper glucose limit (g/L) | prior to induction (h) | At induction point | At the end of ferm. | WCW (g/L) | DCW (%) | Total proteins (mg/g biomass) | expression (%) from total proteins |
|---|---|---|---|---|---|---|---|---|---|---|
| M-83 | 5.1 | 2.2 | 17 | 11.25 | 94.6 | 136.2 | 169.1 | 30.12 | 115.00 | 18.95 |
| M-84 | 4.9 | 2.2 | 22 | 11.25 | 91.8 | 139.2 | 161.4 | 31.89 | 98.33 | 18.95 |
| M-85 | 5.6 | 2.7 | 17 | 11.75 | 95.8 | 149.3 | 158.5 | 30.98 | 101.33 | 17.95 |
| M-86 | 5.4 | 2.7 | 22 | 11.50 | 91.6 | 147.0 | 170.7 | 30.26 | 113.33 | 17.35 |
| M-80 | 5.3 | 3.0 | 22 | 11.75 | 103.6* | 180.6* | 175.4 | 32.11 | 120.33 | 18.53 |
| M-81 | 5.2 | 3.0 | 22 | 11.00 | 96.8* | 184.0* | 185.9 | 33.47 | 122.20 | 18.47 |
| M-92 | 4.8 | 3.2 | 22 | 11.50 | 103.6 | 172.5 | 188.3 | 30.31 | 112.00 | 20.00 |
| M-82 | 5.5 | 3.4 | 22 | 11.50 | 99.5* | 184.6* | 178.8 | 32.08 | 116.00 | 18.13 |
| M-87 | 4.5 | 3.7 | 17 | 11.75 | 99.6 | 179.0 | 183.4 | 30.82 | 114.33 | 18.75 |
| M-88 | 5.0 | 3.7 | 22 | 11.75 | 96.0 | 158.5 | 175.3 | 30.49 | 116.33 | 18.40 |
| M-89 | 4.8 | 4.2 | 17 | 13.00 | 92.4 | 173.5 | 182.4 | 31.09 | 126.70 | 21.45 |
| M-90 | 4.5 | 4.2 | 22 | 11.75 | 98.8 | 178.0 | 194.1 | 30.67 | 151.00 | 20.95 |

*In earlier performed batches OD measured with BioPhotometer (Eppendorf, Á = 595 nm), other - with Spectrometer EZ 150 (PerkinElmer, A = 600 nm);
WCW: wet cell weight (g/L cell suspension);
DCW: dry cell weight (%).

TABLE 3

Biosynthesis and refolding parameters at different concentrations of microelements

| | $\mu$ | | Micro-elements stock sol. | Total micro-elements | Total micro-elements (mL/L susp.) | hIFNa5 | RP-HPLC, % after refolding | | | |
| | | | | | | | | | Acetylated hIFNa5 | |
| Short batch No. | At ind. point | Avg. after ind. | (mL/L carbon feed) | (mL/L/o.u.) (final) | (acc. final vol.) | mg/mL 6M GdHCl | OxidMet hIFNa5 | Correctly folded hIFNa5 | Peak-1 | Peak-2 |
|---|---|---|---|---|---|---|---|---|---|---|
| M-83 | 0.470 | 0.121 | 2.2 | 0.00581 | 0.790 | 1.84 | 12.60 | 50.35 | 3.02 | 4.08 |
| M-84 | 0.457 | 0.139 | 2.2 | 0.00559 | 0.778 | 1.74 | 14.44 | 46.67 | 3.08 | 4.15 |
| M-85 | 0.350 | 0.148 | 2.7 | 0.00627 | 0.935 | 1.95 | 15.48 | 41.10 | 2.93 | 4.38 |
| M-86 | 0.427 | 0.158 | 2.7 | 0.00639 | 0.939 | 1.85 | 5.61 | 52.65 | 3.33 | 4.63 |
| M-80 | 0.563 | 0.185 | 3.0 | 0.00543 | 0.980 | 2.52 | 0 | 62.01 | 4.08 | 5.07 |
| M-81 | 0.578 | 0.214 | 3.0 | 0.00498 | 0.950 | 2.53 | 0 | 60.63 | 4.2 | 4.56 |
| M-92 | 0.497 | 0.170 | 3.2 | 0.00641 | 1.105 | 2.26 | 0 | 66.58 | 4.07 | 5.45 |
| M-82 | 0.452 | 0.194 | 3.4 | 0.00591 | 1.130 | 2.34 | 0 | 59.98 | 4.53 | 5.0 |
| M-87 | 0.433 | 0.181 | 3.7 | 0.00687 | 1.229 | 2.02 | 0 | 63.04 | 5.22 | 5.52 |
| M-88 | 0.575 | 0.163 | 3.7 | 0.00745 | 1.166 | 1.78 | 1.43** | 63.15 | 2.61 | 3.47 |
| F-0030811* | 0.498 | 0.180 | 4.0 | NT | NT | NT | 0 | 48.36 | 7.75 | 7.11*** |
| M-89 | 0.466 | 0.21 | 4.2 | 0.00787 | 1.365 | 1.82 | 0 | 54.06 | 7.25 | 5.99*** |
| M-90 | 0.522 | 0.196 | 4.2 | 0.00788 | 1.403 | 1.68 | 0 | 55.57 | 7.66 | 5.94*** |

*10 L (working volume) fermentation;
**slower growth rate after induction (dilution, because antifoam sensor was out of order, 84 mL of antifoam solution was added).
***formation of additional (unknown) form is observed between the main peak and two peaks of acetylated forms.
NT: Not tested.

As disclosed herein, Table 2 shows the biosynthesis parameters at different concentrations of microelements in the carbon feed solution whereas Table 3 shows the biosynthesis and refolding parameters at different concentrations of microelements.

A number of studies have been performed, such as (i) the dependence of specific culture growth rate ($\mu$) from the concentration of microelements in the carbon feed solution or in the cell suspension; (ii) the dependence of oxidized methionilated hIFNa5 (OxidMet hIFNa5) after refolding and total acetylated hIFNa5 after refolding from the average specific culture growth rate ($\mu$) after induction; (iii) the dependence of hIFNa5 protein post-translational modifications (OxidMet hIFNa5 after refolding, acetylated hIFNa5 after refolding, and correctly folded hIFNa5 after refolding) from the concentration of microelements in the carbon feed solution; and (iv) the dependence of hIFNa5 related forms (acetylated hIFNa5 after refolding and OxidMet hIFNa5 after refolding) from the concentration of microelements in the carbon feed solution or in the cell suspension. Further, all the batches were subjected to RP-HPLC after refolding. From those results, it is evident, that specific culture growth rate ($\mu$) and biomass yield depends on the concentration of microelements in the cultivation medium (Tables 2-3).

In summary, the results obtained show that:
the lowest content of acetylated hIFNa5 is observed at the highest amounts of oxidized methionilated hIFNa5 and viceversa (short batches No. M-83, M-84, M-85 and M-86);
the amount of acetylated hIFNa5 is about 8-11% when concentration of microelements (stock solution) is within the limits of 3.0-3.7 mL/L carbon feed solution (short batches No. M-80, M-81, M-92, M-82 and M-87) or within the limits of 0.95-1.23 mL/L real final suspension volume (Table 3); and
when the concentration of microelements in the carbon feed solution is higher than 4 mL/L or higher than 1.23 mL/L real final cell suspension volume, an additional unknown (not identified) form was detected [it is observed after the main peak and two peaks of acetylated forms (data not shown)].

The results obtained also show that the upper limit (17 g/L or 22 g/L) of glucose concentration practically does not affect on the quality of the target protein (hIFNa5) and biomass yield, real obtained values were in the limits of error (Table 2).

CONCLUSIONS

Results obtained during this study serves as justification of the microelements concentration in the carbon feed solution and the glucose concentration in the biosynthesis process of recombinant hIFNa5.

Oxidized methionilated hIFNa5 protein is eliminated when the concentration of microelements is equal to or higher than 3.0 mL/L carbon feed solution or higher than 0.95 mL/L real final suspension volume and the average specific culture growth rate ($\mu$) after induction is equal to or higher than 0.17.

Acetylated hIFNa5 protein is about 8-11% when the concentration of microelements is within the limits of about 3.0 to about 3.7 mL/L carbon feed solution or about 0.95 to about 1.23 mL/L real final suspension volume.

When the concentration of microelements in the carbon feed solution is higher than 3.7 mL/L or it is more than 1.23 mL/L real final suspension volume, an unknown (not identified) protein form is synthesized.

Optimal concentration of microelements determining maximal yield and the best quality of the target hIFNa5 protein is within the limits of about 3.0 to about 3.7 mL/L carbon feed solution.

The glucose concentration in the range from 17 g/L to 22 g/L practically does not affect the quality of the target protein (recombinant hIFNa5) and biomass yield.

The invention claimed is:

1. A process for producing an interferon alpha 5 (IFNa5) protein by expression in an *Escherichia coli* host cell which comprises:
   a) providing an IFNa5 producing *E. coli* host cell;
   b) culturing the IFNa5 producing *E. coli* host under conditions effective to express said IFNa5 protein by said recombinant IFNa5 producing *E. coli* host cell in a fermentation medium, with the addition of a carbon feed solution, wherein
      said fermentation medium is free of components from animal origin or yeast origin, and
      said carbon feed solution comprises a carbon source and from about 90 to about 111 mg iron (III) chloride hexahydrate, from about 12.15 to about 14.985 mg calcium chloride dihydrate, from about 20.25 to about 24.975 mg zinc (II) sulfate heptahydrate, from about 4.5 to about 5.55 mg manganese (II) sulfate monohydrate, from about 9 to about 11.1 mg copper (II) sulfate pentahydrate, from about 3.42 to about 4.218 mg cobalt (II) chloride hexahydrate, from about 0.9 to about 1.11 mg sodium molybdate dihydrate and from about 2.07 to about 2.553 mg boric acid per liter of added carbon feed solution; and
   c) isolating, and optionally purifying, the expressed IFNa5 protein,
   wherein said addition of carbon feed solution results in a concentration from about 28.5 to about 36.9 mg iron (III) chloride hexahydrate, from about 3.8475 to about 4.9815 mg calcium chloride dihydrate, from about 6.4125 to about 8.3025 mg zinc (II) sulfate heptahydrate, from about 1.425 to about 1.845 mg manganese (II) sulfate monohydrate, from about 2.85 to about 3.69 mg copper (II) sulfate pentahydrate, from about 1.083 to about 1.4022 mg cobalt (II) chloride hexahydrate, from about 0.285 to about 0.369 mg sodium molybdate dihydrate and from about 0.6555 to about 0.8487 mg boric acid per liter of said fermentation medium.

2. The process according to claim 1, wherein the *E. coli* host cell is transformed with a vector comprising a sequence encoding an IFNa5 protein under the control of an inducible promoter.

3. The process according to claim 1, wherein the *E. coli* host cell is an *E. coli* protease deficient strain.

4. The process according to claim 3, wherein the *E. coli* host cell is an *E. coli* Ion⁻/ompT⁻ protease deficient host strain.

5. The process according to claim 3, wherein the *E. coli* host cell is an *E. coli* BL21 strain.

6. The process according to claim 5, wherein the *E. coli* BL21 strain is an *E. coli* BL21 (DE3) strain.

7. The process according to claim 3, wherein the *E. coli* host cell is an *E. coli* BL21 (DE3) strain and the conditions of step b) comprise induction with isopropyl-β-D-1-thiogalactopyranoside (IPTG).

8. The process according to claim 7, wherein the average specific culture growth rate (µ) after induction is equal to or higher than 0.17.

9. The process according to claim 1, wherein said IFNa5 protein is hIFNa5.

10. The process according to claim 1, wherein the IFNa5 protein comprises the amino acid sequence of SEQ ID NO: 1.

11. The process according to claim 1, wherein the IFNa5 protein is isolated from a mixture comprising said IFNa5 protein in the form of inclusion bodies (IBs) by subjecting said IBs to solubilization to render a mixture containing denatured IFNa5 which is later subjected to an oxidizing renaturation treatment to render a mixture comprising renatured IFNa5 and then subjecting said mixture comprising renatured IFNa5 to a purification process in order to obtain the purified IFNa5.

12. The process according to claim 11, wherein the mixture comprising renatured IFNa5 is purified by subjecting said mixture to a 4-step chromatographic treatment comprising:
    1) subjecting said mixture comprising renatured IFNa5 to a hydrophobic interaction chromatography;
    2) subjecting the solution obtained at step 1) to an anion-exchange chromatography;
    3) subjecting the solution obtained at step 2) to a first cation-exchange chromatography; and
    4) subjecting the solution obtained at step 3) to a second cation-exchange chromatography, wherein said solution is, optionally, diluted with a buffer comprising methionine.

13. The process according to claim 8, wherein the amount of oxidized-Met IFNa5 after refolding is 1% or lower.

14. The process according to claim 2, wherein the *E. coli* host cell is an *E. coli* protease deficient strain.

15. The process according to claim 14, wherein the *E. coli* host cell is an *E. coli* Ion⁻/ompT⁻ protease deficient host strain.

16. The process according to claim 14, wherein the *E. coli* host cell is an *E. coli* BL21 strain.

17. The process according to claim 14, wherein the *E. coli* host cell is an *E. coli* BL21 (DE3) strain.

18. The process according to claim 14, wherein the *E. coli* host cell is an *E. coli* BL21 (DE3) strain and the conditions of step b) comprise induction with IPTG.

19. The process according to claim 18, wherein the average specific culture growth rate (µ) after induction is equal to or higher than 0.17.

20. The process according to claim 19, wherein the amount of oxidized-Met IFNa5 after refolding is 1% or lower.

* * * * *

SEQUENCE LISTING

<160> NUMBER OF SEQ ID NOS: 6

<210> SEQ ID NO 1
<211> LENGTH: 167
<212> TYPE: PRT
<213> ORGANISM: Homo sapiens

<400> SEQUENCE: 1

```
Met Cys Asp Leu Pro Gln Thr His Ser Leu Ser Asn Arg Arg Thr Leu
1               5                   10                  15

Met Ile Met Ala Gln Met Gly Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Thr Trp Asp Glu
65                  70                  75                  80

Thr Leu Leu Asp Lys Phe Tyr Thr Glu Leu Tyr Gln Gln Leu Asn Asp
                85                  90                  95

Leu Glu Ala Cys Met Met Gln Glu Val Gly Val Glu Asp Thr Pro Leu
            100                 105                 110
```

```
Met Asn Val Asp Ser Ile Leu Thr Val Arg Lys Tyr Phe Gln Arg Ile
        115                 120                 125
Thr Leu Tyr Leu Thr Glu Lys Lys Tyr Ser Pro Cys Ala Trp Glu Val
    130                 135                 140
Val Arg Ala Glu Ile Met Arg Ser Phe Ser Leu Ser Ala Asn Leu Gln
145                 150                 155                 160
Glu Arg Leu Arg Arg Lys Glu
                165

<210> SEQ ID NO 2
<211> LENGTH: 33
<212> TYPE: DNA
<213> ORGANISM: Artificial Sequence
<220> FEATURE:
<223> OTHER INFORMATION: Synthetic Construct

<400> SEQUENCE: 2
ggaattccat atgtgtgatc tgcctcagac cca                               33

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
cgggatcctt gaaccagttt tcattccttc                                  30

<210> SEQ ID NO 4
<211> LENGTH: 87
<212> TYPE: DNA
<213> ORGANISM: Artificial Sequence
<220> FEATURE:
<223> OTHER INFORMATION: Synthetic Construct

<400> SEQUENCE: 4
catatgtgtg atctgccgca gacccactcc ctgtctaacc gtcgtactct gatgatcatg   60
gcacagatgg gtcgtatctc tccttc                                      87

<210> SEQ ID NO 5
<211> LENGTH: 37
<212> TYPE: DNA
<213> ORGANISM: Artificial Sequence
<220> FEATURE:
<223> OTHER INFORMATION: Synthetic Construct

<400> SEQUENCE: 5
ctgcagttat tccttacgac gtaaacgttc ttgcaag                          37

<210> SEQ ID NO 6
<211> LENGTH: 504
<212> TYPE: DNA
<213> ORGANISM: E. coli

<400> SEQUENCE: 6
atgtgtgatc tgccgcagac ccactccctg tctaaccgtc gtactctgat gatcatggca   60
cagatgggtc gtatctctcc tttctcctgc ctgaaggaca acatgacttt tggatttcct  120
caggaggagt tgatggcaa ccagttccag aaggctcaag ccatctctgt cctccatgag  180
atgatccagc agaccttcaa tctcttcagc acaaaggact catctgctac ttgggatgag  240
acacttctag acaaattcta cactgaactt taccagcagc tgaatgacct ggaagcctgt  300
```

-continued

```
atgatgcagg aggttggagt ggaagacact cctctgatga atgtggactc tatcctgact    360
gtgagaaaat actttcaaag aatcactctc tatctgacag agaagaaata cagcccttgt    420
gcatgggagg ttgtcagagc agaaatcatg agatccttct ctttatcagc aaacttgcaa    480
gaacgtttac gtcgtaagga ataa                                           504
```